United States Patent
Smith, III et al.

(10) Patent No.: US 9,333,151 B2
(45) Date of Patent: *May 10, 2016

(54) HOME CARE ARTICLES AND METHODS

(75) Inventors: Edward Dewey Smith, III, Mason, OH (US); Shawn David McConaughy, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 437 days.

This patent is subject to a terminal disclaimer.

(21) Appl. No.: 13/439,345

(22) Filed: Apr. 4, 2012

(65) Prior Publication Data

US 2012/0246852 A1    Oct. 4, 2012

Related U.S. Application Data

(60) Provisional application No. 61/471,628, filed on Apr. 4, 2011, provisional application No. 61/523,824, filed on Aug. 15, 2011.

(51) Int. Cl.
| | | |
|---|---|---|
| *A47K 7/02* | (2006.01) | |
| *A61K 8/02* | (2006.01) | |
| *A61Q 5/02* | (2006.01) | |
| *A61Q 9/02* | (2006.01) | |
| *A61Q 19/00* | (2006.01) | |
| *A61Q 19/10* | (2006.01) | |

(52) U.S. Cl.
CPC ............. *A61K 8/0208* (2013.01); *A61Q 5/02* (2013.01); *A61Q 9/02* (2013.01); *A61Q 19/002* (2013.01); *A61Q 19/10* (2013.01)

(58) Field of Classification Search
CPC .......... A61Q 5/02; A61Q 9/02; A61Q 19/10; A61Q 19/002; A61K 8/0208; A61K 8/0204
USPC ...................................... 401/201; 15/104.93
See application file for complete search history.

(56) References Cited

U.S. PATENT DOCUMENTS

| | | |
|---|---|---|
| 2,438,091 A | 3/1948 | Lynch |
| 2,528,378 A | 10/1950 | Mannheimer |
| 2,658,072 A | 11/1953 | Kosmin |
| 3,689,437 A | 9/1972 | McLaughlin |
| 3,949,137 A | 4/1976 | Akrongold |
| 4,181,632 A | 1/1980 | Schebece |
| 4,190,550 A | 2/1980 | Campbell |
| 4,207,198 A | 6/1980 | Kenkare |
| 4,328,131 A | 5/1982 | Carson, Jr. et al. |
| 4,335,025 A | 6/1982 | Barker et al. |
| 4,367,999 A | 1/1983 | Benuzzi |
| 4,510,641 A | 4/1985 | Morris |

(Continued)

FOREIGN PATENT DOCUMENTS

| | | |
|---|---|---|
| CN | 1046273 | 10/1990 |
| CN | 1117835 | 3/1996 |

(Continued)

OTHER PUBLICATIONS

International Search Report, International Application No. PCT/US2012/032123, mailed Jun. 25, 2012, 4 pages.

(Continued)

*Primary Examiner* — Jennifer C Chiang

(57) ABSTRACT

A home care article can include a composition and a substrate. The article can be compliant to a surface.

38 Claims, 3 Drawing Sheets

(56) References Cited

U.S. PATENT DOCUMENTS

| | | |
|---|---|---|
| 4,515,703 A | 5/1985 | Haq |
| 4,554,097 A | 11/1985 | Schebece et al. |
| 4,603,069 A | 7/1986 | Haq et al. |
| 4,654,158 A | 3/1987 | Shepherd |
| 4,665,580 A | 5/1987 | Morris |
| 4,735,739 A | 4/1988 | Floyd et al. |
| 4,812,253 A | 3/1989 | Small et al. |
| 4,861,508 A | 8/1989 | Wegener et al. |
| 4,935,158 A | 6/1990 | Aszman et al. |
| 4,953,250 A | 9/1990 | Brown |
| 4,987,632 A | 1/1991 | Rowe et al. |
| 5,066,494 A | 11/1991 | Becher |
| 5,108,642 A | 4/1992 | Aszman et al. |
| 5,132,115 A | 7/1992 | Wolter et al. |
| 5,139,705 A | 8/1992 | Wittpenn, Jr. et al. |
| 5,225,097 A | 7/1993 | Kacher et al. |
| 5,227,086 A | 7/1993 | Kacher et al. |
| 5,262,079 A | 11/1993 | Kacher et al. |
| 5,264,144 A | 11/1993 | Moroney et al. |
| 5,264,145 A | 11/1993 | French et al. |
| 5,308,180 A | 5/1994 | Pournoor et al. |
| 5,312,559 A | 5/1994 | Kacher et al. |
| RE34,692 E | 8/1994 | Becher |
| 5,340,492 A | 8/1994 | Kacher et al. |
| 5,387,362 A | 2/1995 | Tollens et al. |
| 5,393,466 A | 2/1995 | Ilardi et al. |
| 5,433,883 A | 7/1995 | Massaro et al. |
| 5,433,894 A | 7/1995 | Massaro et al. |
| 5,482,643 A | 1/1996 | Chambers et al. |
| 5,487,884 A | 1/1996 | Bissett et al. |
| 5,520,840 A | 5/1996 | Massaro et al. |
| 5,523,017 A | 6/1996 | Moran et al. |
| 5,540,854 A | 7/1996 | Fair et al. |
| 5,652,228 A | 7/1997 | Bissett |
| 5,681,852 A | 10/1997 | Bissett |
| 5,683,971 A | 11/1997 | Rose et al. |
| 5,683,973 A | 11/1997 | Post et al. |
| 5,698,475 A | 12/1997 | Vlasblom |
| 5,702,992 A | 12/1997 | Martin et al. |
| 5,703,025 A | 12/1997 | Zyngier et al. |
| 5,704,723 A | 1/1998 | Salisian |
| 5,756,438 A | 5/1998 | Rau et al. |
| 5,786,311 A | 7/1998 | Zyngier et al. |
| 5,824,296 A | 10/1998 | Dubief et al. |
| 5,888,953 A | 3/1999 | Harris et al. |
| 5,916,856 A | 6/1999 | Massaro et al. |
| 5,968,852 A | 10/1999 | Vlasblom |
| 5,972,860 A | 10/1999 | Eshita et al. |
| 5,985,808 A | 11/1999 | He et al. |
| 6,026,534 A | 2/2000 | Gonda et al. |
| 6,028,042 A | 2/2000 | Chambers et al. |
| 6,063,390 A | 5/2000 | Farrell et al. |
| 6,074,997 A | 6/2000 | Rau et al. |
| 6,153,208 A | 11/2000 | McAtee et al. |
| 6,162,457 A | 12/2000 | Martz |
| 6,206,863 B1 | 3/2001 | Skewes et al. |
| 6,217,854 B1 | 4/2001 | Farrell et al. |
| 6,245,343 B1 | 6/2001 | Roulier et al. |
| 6,322,801 B1 | 11/2001 | Lorenzi et al. |
| 6,328,811 B1 | 12/2001 | Martin et al. |
| 6,376,046 B1 | 4/2002 | Hoshino et al. |
| 6,391,835 B1 | 5/2002 | Gott et al. |
| 6,395,691 B1 | 5/2002 | Tsaur |
| 6,428,799 B1 | 8/2002 | Cen et al. |
| 6,467,981 B1 | 10/2002 | Gueret |
| 6,491,928 B1 * | 12/2002 | Smith, III ................ 424/401 |
| 6,491,933 B2 | 12/2002 | Lorenzi et al. |
| 6,491,937 B1 | 12/2002 | Slavtcheff et al. |
| 6,547,468 B2 | 4/2003 | Gruenbacher et al. |
| 6,550,092 B1 | 4/2003 | Brown et al. |
| 6,607,739 B1 | 8/2003 | Wallo |
| 6,638,527 B2 | 10/2003 | Gott et al. |
| 6,638,611 B2 | 10/2003 | Seth |
| 6,645,611 B2 | 11/2003 | Seth |
| 6,677,294 B2 | 1/2004 | Shaw et al. |
| 6,730,317 B2 | 5/2004 | Gueret |
| 6,753,063 B1 | 6/2004 | Pung et al. |
| 6,783,294 B2 | 8/2004 | Duden et al. |
| 6,835,701 B2 | 12/2004 | Seipel et al. |
| 6,867,380 B2 | 3/2005 | Miki et al. |
| 6,878,380 B2 | 4/2005 | Farrell et al. |
| 6,883,353 B2 | 4/2005 | Goldoni et al. |
| 6,902,338 B2 | 6/2005 | Puvvada et al. |
| 6,903,057 B1 | 6/2005 | Tsaur |
| 6,977,238 B1 | 12/2005 | Wetzel et al. |
| 6,992,054 B2 | 1/2006 | Lee et al. |
| 7,033,064 B2 | 4/2006 | Ida |
| 7,033,964 B2 | 4/2006 | Gillette |
| 7,101,612 B2 | 9/2006 | Lang et al. |
| 7,115,535 B1 * | 10/2006 | Smith et al. ................ 442/123 |
| 7,115,551 B2 | 10/2006 | Hasenoehrl et al. |
| 7,229,956 B2 | 6/2007 | Bedford et al. |
| 7,276,459 B1 | 10/2007 | Lang et al. |
| 7,288,513 B2 | 10/2007 | Taylor et al. |
| 7,320,953 B2 | 1/2008 | Grissett et al. |
| 7,335,626 B2 | 2/2008 | Keenan et al. |
| 7,345,014 B2 | 3/2008 | Keenan et al. |
| 7,348,299 B2 | 3/2008 | Keenan et al. |
| 7,381,692 B2 | 6/2008 | Grissett et al. |
| 7,381,693 B2 | 6/2008 | Keenan et al. |
| 7,419,321 B2 | 9/2008 | Tereschouk |
| 7,452,547 B2 | 11/2008 | Lambino et al. |
| 7,462,348 B2 | 12/2008 | Gruenbacher et al. |
| 7,514,071 B2 | 4/2009 | Simon et al. |
| 7,581,273 B2 | 9/2009 | Dobrin et al. |
| 7,584,519 B2 | 9/2009 | Ouellette et al. |
| 7,651,290 B2 | 1/2010 | Bauer et al. |
| 7,674,058 B2 | 3/2010 | Berger Sharp et al. |
| 7,846,462 B2 | 12/2010 | Spadini et al. |
| 7,874,756 B2 | 1/2011 | Nuebel et al. |
| 8,147,853 B2 | 4/2012 | Taylor et al. |
| 8,157,464 B2 | 4/2012 | Prax |
| 8,308,388 B2 | 11/2012 | Guay |
| 8,357,383 B2 | 1/2013 | Spadini et al. |
| 8,475,817 B2 | 7/2013 | Hasenoehrl et al. |
| 8,534,947 B2 | 9/2013 | Prax |
| 2001/0003565 A1 | 6/2001 | Mcosker et al. |
| 2001/0028894 A1 | 10/2001 | Gueret |
| 2002/0178507 A1 | 12/2002 | Goldoni et al. |
| 2002/0192268 A1 | 12/2002 | Alwattari et al. |
| 2003/0079323 A1 | 5/2003 | Ngai |
| 2003/0140439 A1 | 7/2003 | Durden et al. |
| 2003/0143263 A1 | 7/2003 | Durden et al. |
| 2003/0180242 A1 | 9/2003 | Eccard et al. |
| 2003/0194425 A1 | 10/2003 | Simon et al. |
| 2003/0203010 A1 | 10/2003 | Wallo |
| 2003/0228352 A1 | 12/2003 | Hasenoehrl et al. |
| 2004/0116017 A1 | 6/2004 | Smith, III et al. |
| 2004/0147189 A1 | 7/2004 | Smith, III et al. |
| 2004/0170670 A1 | 9/2004 | Smith et al. |
| 2004/0175343 A1 | 9/2004 | Osborne et al. |
| 2004/0176002 A1 | 9/2004 | Siegwart |
| 2004/0237234 A1 | 12/2004 | Young et al. |
| 2004/0237235 A1 | 12/2004 | Visioli et al. |
| 2005/0148260 A1 | 7/2005 | Kopacz et al. |
| 2005/0202068 A1 | 9/2005 | Hasenoehrl et al. |
| 2005/0276827 A1 | 12/2005 | Macedo et al. |
| 2005/0276828 A1 | 12/2005 | Grissett et al. |
| 2006/0097170 A1 | 5/2006 | Prinz et al. |
| 2006/0135026 A1 | 6/2006 | Arendt et al. |
| 2006/0141014 A1 | 6/2006 | Eknoian et al. |
| 2006/0246119 A1 | 11/2006 | Eknoian et al. |
| 2007/0048359 A1 | 3/2007 | Bolton |
| 2007/0071797 A1 | 3/2007 | Hernandez-Munoa et al. |
| 2007/0099813 A1 | 5/2007 | Luizzi et al. |
| 2007/0130706 A1 | 6/2007 | Buhrow et al. |
| 2007/0130707 A1 | 6/2007 | Cohen et al. |
| 2007/0283516 A1 | 12/2007 | Rasmussen et al. |
| 2008/0104787 A1 | 5/2008 | Keenan et al. |
| 2008/0116096 A1 | 5/2008 | Johnson et al. |
| 2008/0145388 A1 | 6/2008 | Roreger et al. |
| 2008/0168748 A1 | 7/2008 | McCloskey |
| 2008/0247806 A1 * | 10/2008 | Todd et al. ................ 401/205 |
| 2008/0299269 A1 | 12/2008 | Mane et al. |

(56) References Cited

U.S. PATENT DOCUMENTS

| | | |
|---|---|---|
| 2009/0028808 A1 | 1/2009 | Cetti et al. |
| 2009/0178692 A1 | 7/2009 | Warr et al. |
| 2009/0246376 A1 | 10/2009 | Gunn et al. |
| 2009/0324520 A1 | 12/2009 | Cetti et al. |
| 2010/0130988 A1 | 5/2010 | Bolton |
| 2011/0278429 A1 | 11/2011 | Jha et al. |
| 2011/0290904 A1 | 12/2011 | Mane et al. |
| 2012/0028869 A1 | 2/2012 | Crawford et al. |
| 2012/0246851 A1 | 10/2012 | Smith, III et al. |
| 2012/0246852 A1 | 10/2012 | Smith, III et al. |
| 2012/0252715 A1 | 10/2012 | McConaughy et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0118518 A1 | 5/2013 | Spadini et al. |
| 2013/0266622 A1 | 10/2013 | Mcconnaughy et al. |
| 2015/0000057 A1 | 1/2015 | McConaughy et al. |
| 2015/0000058 A1 | 1/2015 | McConaugy et al. |
| 2015/0005223 A1 | 1/2015 | McConaughy et al. |

FOREIGN PATENT DOCUMENTS

| | | |
|---|---|---|
| CN | 1318622 | 10/2001 |
| DE | 19744213 | 4/1999 |
| DE | 20017205 | 12/2000 |
| DE | 20304298 | 6/2003 |
| DE | 10301838 | 7/2004 |
| DE | 202004007851 | 8/2004 |
| EP | 0032793 B1 | 3/1984 |
| EP | 0047116 B1 | 7/1985 |
| EP | 0161911 | 11/1985 |
| EP | 0211664 | 2/1987 |
| EP | 0272492 A2 | 6/1988 |
| EP | 0353013 | 1/1990 |
| EP | 387693 | 9/1990 |
| EP | 387694 | 9/1990 |
| EP | 0863201 A2 | 9/1998 |
| EP | 1000605 A2 | 5/2000 |
| EP | 1106165 | 6/2001 |
| EP | 1153554 A1 | 11/2001 |
| EP | 2105061 | 9/2009 |
| FR | 1 190 521 A | 10/1959 |
| FR | 2822045 | 9/2002 |
| FR | 2855741 | 12/2004 |
| GB | 2163947 A | 3/1986 |
| GB | 2222526 A | 3/1990 |
| JP | 61277608 A2 | 12/1986 |
| JP | 02265516 | 10/1990 |
| JP | 08084684 | 4/1996 |
| JP | 09299271 | 11/1997 |
| JP | 10000170 | 1/1998 |
| JP | 10183194 A1 | 7/1998 |
| JP | 2002142857 | 5/2002 |
| JP | 2002275031 | 9/2002 |
| JP | 2002315689 | 10/2002 |
| JP | 2004016560 | 1/2004 |
| JP | 2004236996 | 8/2004 |
| JP | 2006082263 | 3/2006 |
| JP | 2006130194 | 5/2006 |
| JP | 2009292750 | 12/2009 |
| JP | 2010046129 | 3/2010 |
| SE | 8703015 | 2/1989 |
| WO | 95/00116 | 1/1995 |
| WO | 95/11887 | 5/1995 |
| WO | 95/26710 A1 | 10/1995 |
| WO | 96/31187 A2 | 10/1996 |
| WO | 97/04683 | 2/1997 |
| WO | 98/27193 A1 | 6/1998 |
| WO | 2009/828399 A1 | 7/1998 |
| WO | 99/31184 | 6/1999 |
| WO | 01/08655 A1 | 2/2001 |
| WO | 01/08658 A1 | 2/2001 |
| WO | 2006/036976 | 4/2006 |
| WO | 2008/113973 A1 | 9/2008 |

OTHER PUBLICATIONS

Photographs of Johnson's Super Sudzer c-z grip soap purchased from Kroger stores around Aug. 2010 and believed to have been on the market in the US at least a year before the filing date of this application.

Photographs of Johnson's Buddies, easy-grip sudzing bar purchased from Target stores around Aug. 2010 and believed to have been on the market in the US at least a year before the filing date of this application.

U.S. Appl. No. 29/459,273, Jun. 27, 2013, Althaus.

U.S. Appl. No. 29/459,274, Jun. 27, 2013, Althaus.

International Search Report and Written Opinion of the Internatinal Searching Authority, PCT/US2012/032123, mailed Jun. 25, 2012, 11 pages.

PCT International Search Report and Written Opinion for PCT/US2012/032054 dated Jul. 4, 2012.

PCT International Search Report and Written Opinion for PCT/US2012/032111 dated Dec. 17, 2012.

International Search Report and Written Opinion of PCT/US00/01387 dated Sep. 20, 2000.

International Search Report and Written Opinion of PCT/US2012/050873 dated Dec. 10, 2012.

International Search Report and Written Opinion of PCT/US2012/050874 dated Dec. 12, 2012.

International Search Report and Written Opinion of PCT/US2012/050877 dated Dec. 6, 2012.

* cited by examiner

HOME CARE ARTICLES AND METHODS

CROSS REFERENCE TO RELATED APPLICATIONS

This application claims priority to provisional application No. 61/471,628 filed Apr. 4, 2011 and provisional application No. 61/523,824 filed Aug. 15, 2011, both of which are incorporated herein by reference.

FIELD OF THE INVENTION

The present disclosure generally relates to home care articles and methods relating thereto.

BACKGROUND OF THE INVENTION

Surface cleaning with liquid detergents poses an ongoing problem for consumers. Consumers utilizing liquid detergents as a light-duty liquid dishwashing cleansing composition or as a hard surface cleansing composition frequently find removal of soil, food and other residues difficult. As such, consumers typically couple the cleansing composition with implements such as a washcloth, sponge, brush or some other implement to physically remove the soil from the target surface.

Although a consumer's experience with a cleansing composition can be enhanced by coupling the cleansing composition with an implement, to date, such an experience has not been completely ideal. For example, coupling such cleansing compositions with an implement tends to lead to clutter in the kitchen or bathroom as a consumer needs to carry or store cumbersome bottles of cleansing products and the implements themselves. Additionally, coupling requires the user to perform additional steps of applying the cleansing composition on the implement and then rubbing or wiping the implement on the target surface rather than just applying the cleansing composition directly. As such, more water tends to be consumed and increases the waste and carbon footprint of the consumer.

Some attempts have been made to combine an implement with a cleansing composition in a home care cleansing article. However, these executions were not ideal. For example, the rigidity of some articles does not allow for the article to easily conform to the surface to which it is applied and makes it difficult to thoroughly clean the target surface. Some other attempts at a more conformable product did not provide a desired reusability and tended to create additional waste. In particular, such cleansing articles tend to lack durability and/or include cleansing compositions that completely dissolve after very few uses.

Accordingly, it would be desirable to provide a compliant home care article that can have desirable cleansing properties, including suitable sudsing and cleaning characteristics, can conform to the target surface, can be reusable and/or are easy to use.

SUMMARY OF THE INVENTION

In one embodiment, there is a home care article, comprising: a compliant cleansing composition; and a water penetrable first substrate adjacent to the composition; wherein the composition is greater than 3500 wt. %, by weight of the total substrate.

In another embodiment, there is a home cleansing article, comprising: a compliant cleansing composition having a first side and a second side; a first substrate adjacent to one side of the cleansing composition; a second substrate adjacent to the other side of the cleansing composition; a first water insoluble substrate adjacent to the first substrate, and a second water insoluble substrate adjacent to the second substrate; wherein the composition has a compliance of about 0.03 to about 1.50 kg/mm.

In an additional embodiment, there is a compliant home care article, comprising: about 4000 wt. % or more, by weight of total substrate, of a cleansing composition; a first substrate surrounding the cleansing composition and having a water flux rate of about 0.1 $cm^3/cm^2/s$ to about 60 $cm^3/cm^2/s$; and a second substrate surrounding the first substrate and having a water flux rate of about 0.1 $cm^3/cm^2/s$ to about 60 $cm^3/cm^2/s$; wherein the home care article has a consumption rate of about 0.05 g/use to about 20 g/use.

These and other embodiments are more fully described in the description below.

DETAILED DESCRIPTION OF THE INVENTION

I. Definitions

Figure 1:
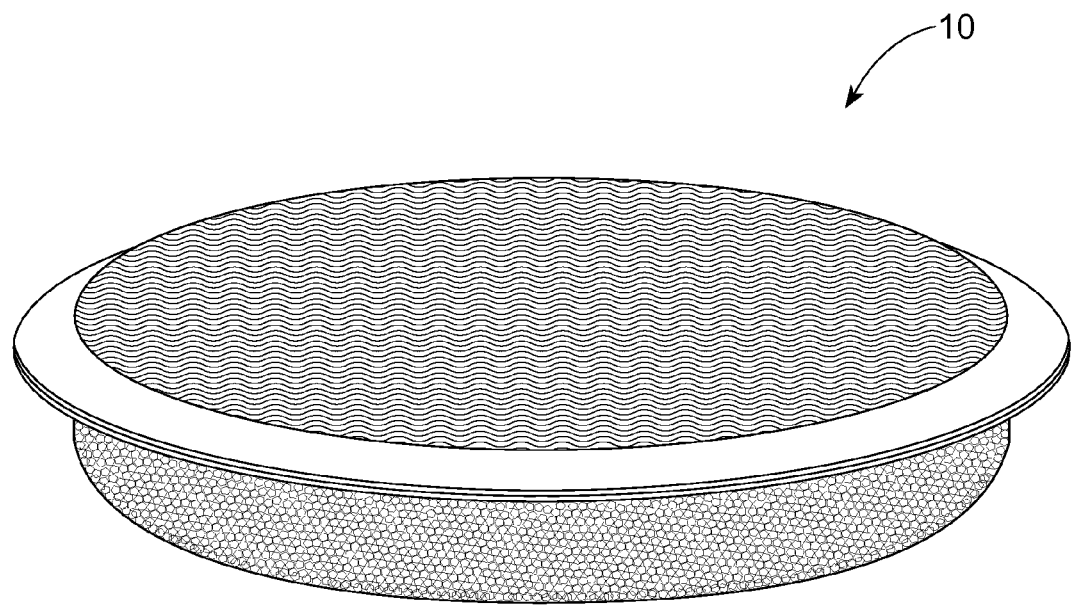
FIG. 1 depicts a perspective view of a home care article according to one embodiment.

As used herein, the following terms shall have the meaning specified thereafter:

"Cleansing composition" refers to compositions intended for application to a target surface such as dishware, countertops, bath tubs, toilets, floors, windows, sinks and the like to remove, for example, food particles, soils, dirt, oil, and the like. The cleansing compositions disclosed herein can be rinse-off formulations, in which the product is applied to the target surface via, for example, an implement or substrate and then subsequently rinsed within seconds to minutes from the target surface with water.

Compliant as used herein refers to an article and/or composition that at least partially conforms to a surface to which it is applied by some degree of deformation.

As used herein "dishware" means a surface such as dishes, glasses, pots, pans, baking dishes and flatware made from ceramic, china, metal, glass, plastic (polyethylene, polypropylene, polystyrene, etc.) and wood.

"g/use" refers to grams per use. This is the unit used for rate of consumption and the method for measuring, and/or calculating it is described below.

"Macroapertured" refers to a substrate containing well-defined apertures having an average diameter of about 300 microns or greater.

"Microapertured" generally refers to a substrate containing well-defined microscopic apertures (i.e., those not readily visible to a naked eye having 20/20 vision).

"Natural" refers to materials that can be derived from plants, animals, insects, or materials that can be byproducts of plants, animals, or insects.

"Nonwoven" refers to a substrate comprising fibers not woven into a fabric but rather formed into a sheet. The fibers can either be random (i.e., randomly aligned) or the fibers can be non-random (for example, the nonwoven can be carded i.e. combed to be oriented in primarily one direction).

"Home care" refers to a composition or article for application to a target surface such as dishware, countertops, bath tubs, toilets, floors, windows, sinks and the like. Home care compositions can be rinse-off formulations, in which the composition can be applied to the target surface and then subsequently rinsed within seconds to minutes of application. The composition could also be wiped off using a substrate. The home care articles or compositions can also be used for cleansing of the target surface.

"Reusable" refers to an article that can be used for a number of usage events, such as showers and/or baths, wherein the number of usage events can be about 5 or greater, about 7 or greater, about 10 or greater, about 15 or greater, about 20 or greater, about 25 or greater, or about 30 or greater.

"Substantially free of" refers to about 5% or less, about 3% or less, about 1% or less, or about 0.1% or less of a stated ingredient. "Free of" refers to no detectable amount of the stated ingredient or thing.

"Substrate" refers to a material which can limit the amount of water to which a cleansing composition is exposed during a usage event versus exposure of a cleasning composition itself absent a substrate. The substrate may be, for example, a film, formed film, batting, woven, nonwoven, or a combination thereof.

As used herein "suds profile" means the amount of sudsing (high or low) and the persistence of sudsing (sustained sudsing) throughout the washing process resulting from the use of the cleansing composition of the present composition. As used herein "high sudsing" refers to cleansing compositions which are both high sudsing (i.e. a level of sudsing considered acceptable to the consumer) and have sustained sudsing (i.e. a high level of sudsing maintained throughout the cleansing operation).

"Synthetic" refers to materials that can be obtained primarily from various man-made materials or from natural materials which have been altered.

"Usage event" refers to one 5 minute cycle of the Consumption Test below.

"Water insoluble substrate" refers to a substrate which does not dissolve in water during the life of the article

II. Home Care Article

A home care article comprises a substrate and a cleansing composition. The home care article may also comprise multiple substrates. The home care article may be used, for example, on a target surface such as dishware, countertops, bath tubs, toilets, floors, windows, sinks and the like. The home care article may also be used, for example, for cleansing of the target surface. In one embodiment, the home care article is a home care cleansing article. In one embodiment, the home care article is reusable.

The home care article can be compliant (i.e. it at least partially conforms to a surface to which it is applied by some degree of deformation.) For example, if the article is a home care article for cleansing the target surface, then the article will bend to some degree to more fully contact a curved surface like a sink, dishware or toilet. Thus, if the home care article is originally flat with no curve, when applied to the target surface for cleansing there would be some amount of bend to better conform to the target surface. Likewise, if the article's shape has a small amount of a curve, when applied to the target surface the article would bend to some degree to more fully contact the target surface. Oppositely, if the original article is curved such that it would not need to bend to conform to a curved target surface, then it would bend to straighten when applied to a less curved surface like the floor or a dish. In one embodiment, the article and/or composition is fully compliant meaning it is capable of completely conforming to the surface to which it is applied.

In some embodiments, the compliant article will comprise a particulate composition. A particulate composition can be made of smaller particles like sand, larger particles like pellets, or anything in-between, and combinations thereof. These compositions may be formless and thus rely on a substrate or substrates to house them for use. For these types of articles, it is the ability of the composition in combination with the substrate(s) to at least partially deform to the shape of the surface to which it is applied that makes them compliant.

In some embodiments, compliance of the article can be measured according to the test described in more detail below. In some embodiments, a home care article can comprise a compliance value of about 1.50 kg/mm or less. In varying embodiments, the compliance value of the article is about 1.35 kg/mm or less; about 1.25 or less; about 1.2 or less; about 1.1 or less; or about 1.0 or less. In additional embodiments, the article has a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; about 0.10 to about 1.1; or any combination thereof.

The home care composition can also be compliant similar to what is discussed above for the article. For example, if the composition is a cleansing composition, then the composition will bend to some degree to more fully contact a curved surface like a sink, dishware or toilet. Thus, if the cleansing composition is originally flat with no curve, when applied to the target surface for cleansing there would be some amount of bend to better conform to the target surface. Likewise, if the composition's shape has a small amount of a curve, when applied to the target surface the composition would bend to some degree to more fully contact the target surface. Oppositely, if the original composition is curved such that it would not need to bend to conform to a curved target surface like the arm, then it would bend to straighten when applied to a less curved surface like the floor or a dish.

In some embodiments, compliance of the composition can be measured according to the test described in more detail below. In some embodiments, a home care composition can comprise a compliance value of about 1.50 kg/mm or less. In varying embodiments, the compliance value of the composition is about 1.35 kg/mm or less; about 1.25 or less; about 1.2 or less; about 1.1 or less; or about 1.0 or less. In additional embodiments, the composition has a compliance of about 0.01 kg/mm to about 1.50 kg/mm; about 0.03 kg/mm to about 1.50 kg/mm; about 0.05 kg/mm to about 1.25 kg/mm; about 0.05 kg/mm to about 1.15 kg/mm; about 0.10 to about 1.1; or any combination thereof.

In some embodiments, the composition and/or article may become compliant after exposure to water. Thus, you may have a non-compliant composition or article that, after exposure to a liquid, like water, during a usage event, becomes compliant. If an article and/or composition become compliant by the end of a second usage event, then they are considered compliant according to this application.

The home care article will have a rate of consumption. This is a measure of how much of the composition is used during a usage event. A method for measuring consumption rate of the article is described in more detail below. In one embodiment, the article will have a consumption rate of about 20 g/use or less. In another embodiment, the article will have a consumption rate of about 15 g/use or less. In alternate embodiments, the article will have a consumption rate of about 1.5 g/use to about 15 g/use; from about 2.5 g/use to about 10 g/use; from about 3.5 g/use to about 6.5 g/use, or any combination thereof.

Figure 4:
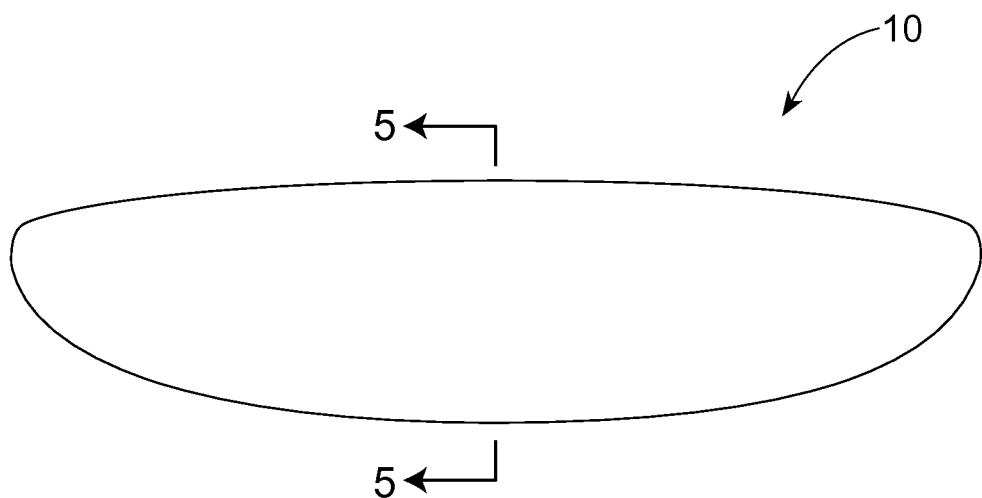
FIG. 4 depicts a side view of a home care article according to another embodiment.
Figure 5A:
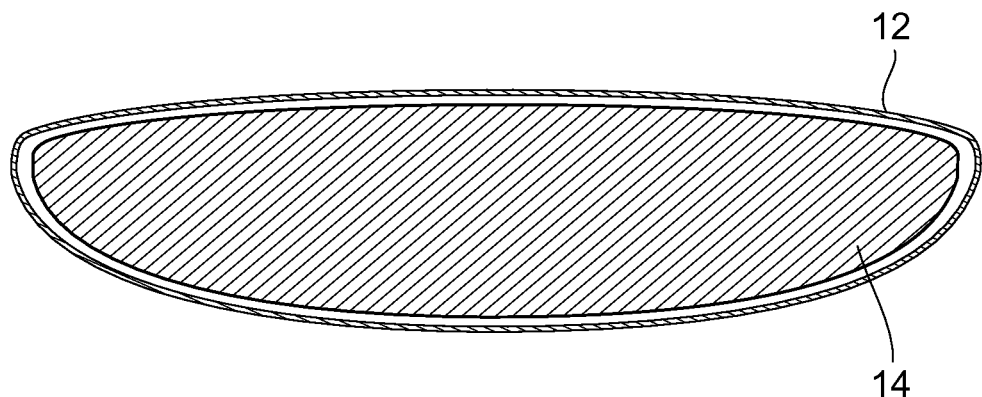
FIG. 5A depicts a cross sectional view of the home care article of FIG. 4, along line 5-5.
Figure 5B:
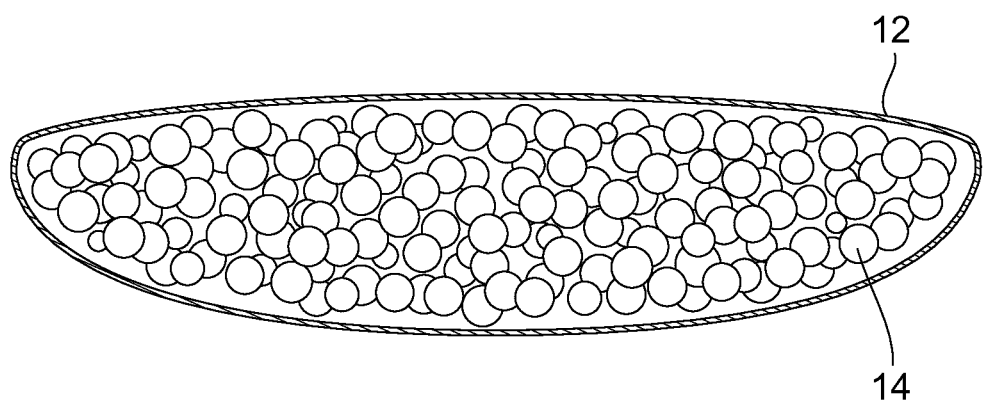
FIG. 5B depicts a cross sectional view of the home care article of FIG. 4, along line 5-5, where the composition is in the form of pellets.

A perspective view of a home care article 10 according to one embodiment is shown in FIG. 1. As shown in FIGS. 4, 5A, and 5B, the home care article 10 can comprise a water penetrable first substrate 12 and a cleansing composition 14, wherein the water penetrable first substrate 12 is adjacent to the cleansing composition 14. The water penetrable first substrate 12 at least partially surrounds the composition 14. In one embodiment, as shown in FIG. 4, a single piece of water penetrable substrate 12 has been wrapped around the cleansing composition 14 and sealed (not shown). In FIG. 5B, the composition 14 is in the form of pellets.

Figure 2:
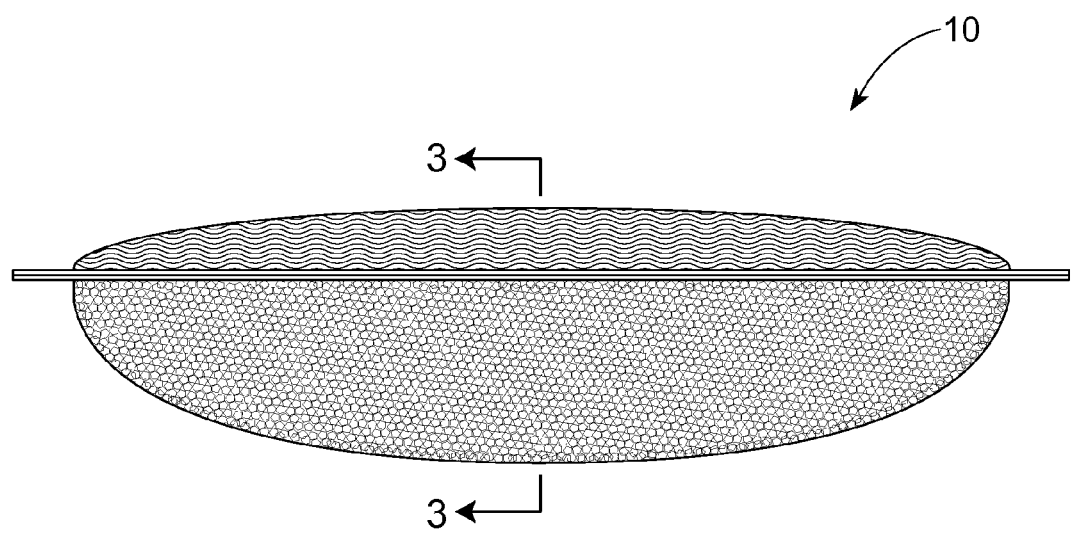
FIG. 2 depicts a side view of a home care article according to one embodiment.
Figure 3A:
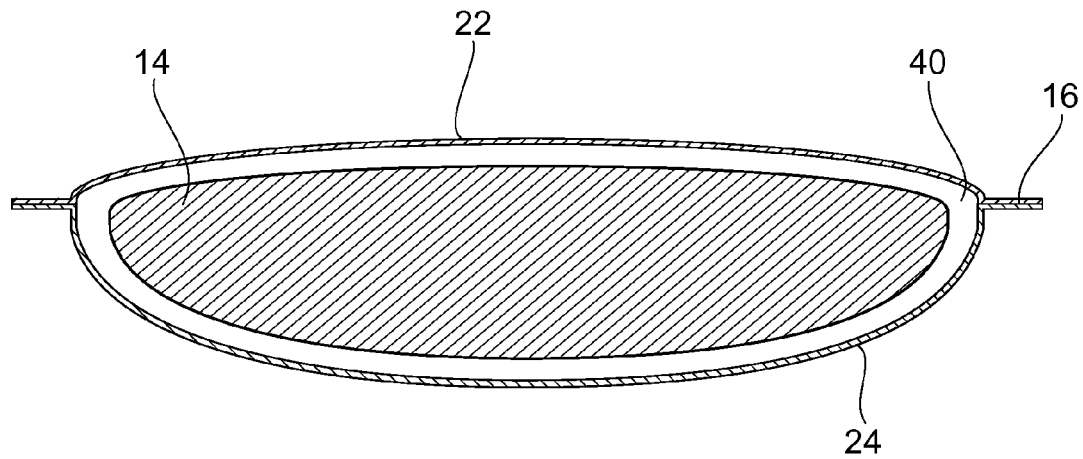
FIG. 3A depicts a cross sectional view of the home care article of FIG. 2, along line 3-3.

In another embodiment, as illustrated in FIGS. 2 and 3A, a home care article 10 comprises a cleansing composition 14, a first substrate 22 adjacent to the cleansing composition 14, and a second substrate 24 adjacent to the cleansing composition 14. In one embodiment depicted in FIG. 3A, the seal 16 joining the first and second substrates (22, 24) is only visible on the ends, but actually goes all the way around the cleansing composition 14. The first and second substrates (22, 24) may, however, may be sealed in other configurations, or, may only be partially sealed so as to form, for example, a pouch. The first and second substrates (22, 24) may be the same or different.

Figure 3B:
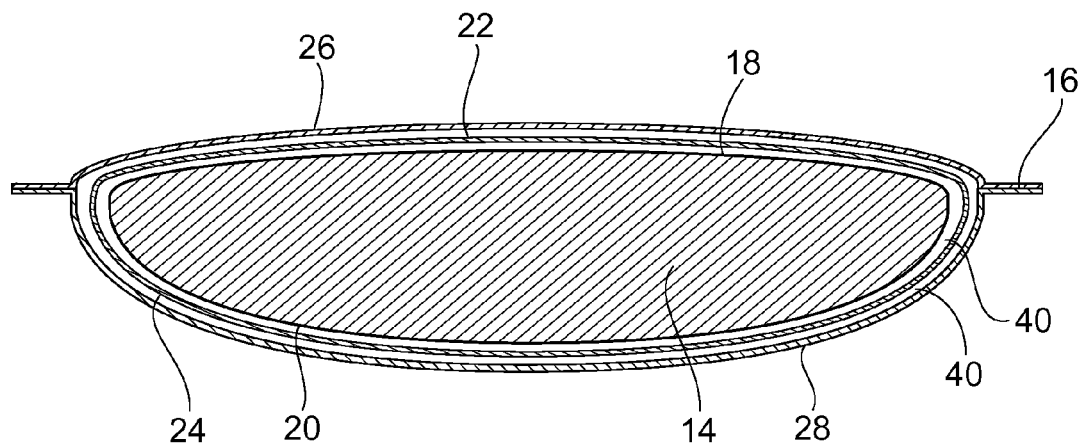
FIG. 3B depicts a cross sectional view of the home care article of FIG. 2, along line 3-3, where additional substrates have been added.

In another embodiment, as illustrated in FIGS. 2 and 3B, a home care article 10 comprises a cleansing composition 14 having a first side 18 and a second side 20. A first substrate 22 is adjacent to the first side 18, while a second substrate 24 is adjacent to the second side 20. In one embodiment depicted in FIG. 4, the seal 16 joining the first and second substrates (22, 24) is only visible on the ends 30, but actually goes all the way around the cleansing composition 14. In addition, a first water insoluble substrate 26 is adjacent to the first substrate 22 and a second water insoluble substrate 28 is adjacent to the second substrate 24. The first and second water insoluble substrates (26, 28) may be the same or different. Like the seal of the first and second substrate (22, 24), while only visible on the ends, the seal 16 of the first and second water insoluble substrates (26, 28) goes all the way around the cleansing composition 14. The seal 16 of the first and second water insoluble substrate (26, 28) may, however, be sealed in other configurations, or, may only be partially sealed so as to form, for example, a pouch.

The home care article may also comprise a chamber 40, as seen, for example, in FIGS. 3A and 3B. A chamber is open area between a substrate and a cleansing composition or between a substrate and another substrate, where the substrate is not touching the cleansing composition or the other substrate. The substrate(s) may be flexible such that they touch the composition (or another substrate) in some areas and not others. The areas where the substrate is touching or not touching the composition or other substrate may shift as the substrate(s) and composition shift during handling and/or use.

The home care article can include from about 0.5% to about 25,000%, by weight of total substrate(s), of a cleansing composition. In one embodiment, the article comprises greater than 3,500%, by weight of the total substrate(s), of a composition. In another embodiment, the article comprises greater than 4,000%, by weight of the total substrate(s), of a composition. In varying embodiments, the article comprises greater than 4,250%, by weight of the total substrate(s), of a composition; greater than 4,500%, by weight of the total substrate(s), of a composition; greater than 4,750%, by weight of the total substrate(s), of a composition; greater than 5,000%, by weight of the total substrate(s), of a composition; or any combination thereof.

The home care article may be in any suitable shape, for example, oval, square, rectangular, circular, triangular, hour glass, hexagonal, c-shaped, etc.

A. Substrate

The home care article comprises at least one substrate. The substrate can enhance cleansing of a target surface such as dishware, countertops, bath tubs, toilets, floors, windows, sinks and the like. For example, by physically coming into contact with the target surface, the substrate can aid in the cleansing and removal of food particles, soils, dirt, oil, and other debris such that the substrate can act as an efficient cleansing implement but can also be non-abrasive to the target surface. A substrate can be a composite (i.e. there are multiple plies to the substrate which may be of the same or different materials). In one embodiment, the substrate is water insoluble. In other embodiments, the substrate is water penetrable.

In one embodiment, a substrate at least partially surrounds a cleansing composition. In another embodiment, a substrate surrounds a cleansing composition. In additional embodiments, a substrate is in the form of a pouch, pocket, wrap, or a combination thereof.

A substrate may be a contact substrate, which is a substrate for contacting a target surface. A substrate may also be a noncontact substrate. Noncontact substrates may, for example, be used to help give a home care article the desired consumption rate, suds profile, etc.

The substrate may be water penetrable. Where the substrate is water penetrable, the substrate will have a water flux rate. The water flux rate can be used to limit wetting of the cleansing composition included in the home care article thereby controlling suds, dissolution, and/or consumption of the composition included in the home care article. Without being limited by theory, the first substrate can manage or limit the water flux rate to provide controlled wetting and to extend a useful life of the home care composition while still enabling enough wetting to provide, for example, suitable suds. In certain embodiments, the water flux rate can be from about 0.1 $cm^3/cm^2/s$ to about 200 $cm^3/cm^2/s$, from about 0.4 $cm^3/cm^2/s$ to about 120 $cm^3/cm^2/s$, from about 20 $cm^3/cm^2/s$ to about 100 $cm^3/cm^2/s$, or any combination thereof, as measured by the water flux rate test disclosed below. The ability to control the water flux rate allows for adjustment such that the composition, like a cleansing composition, can be reused and, thus, last through a number of uses while still exhibiting sudsing characteristics expected by consumers.

In some embodiments, there will be a water flux differential between substrates. In varying embodiments, the flux differential between substrates is at least about 2.5 $cm^3/cm^2/s$; about 3.0 $cm^3/cm^2/s$ or more; or about 4.0 $cm^3/cm^2/s$ or more.

The substrate will, in some embodiments, need a sufficient tensile strength in order to effectively fulfill its desired role. For example, a contact substrate may need to have a higher tensile strength than a noncontact substrate due to its contact with the target surface. In one embodiment, a substrate can provide an ultimate tensile strength of about 10 g/mm width or greater, about 30 g/mm (width) or greater, about 60 g/mm (width) or greater, or about 200 g/mm (width) or greater and a stiffness of about 1 g/mm (width) or greater, about 2 g/mm (width) or greater, about 7 g/mm (width) or greater, about 20 g/mm (width) or greater, or about 80 g/mm (width) or greater.

The substrate can further provide a variety of textures. Texturized substrates can be used for both contact and non-contact substrates. In one embodiment, the article can have a different texture on each side thereof. For example, the article can include a gripping side and a substrate application side. In one embodiment, the gripping side can include a texture that is the same as the substrate application side. In another embodiment, the gripping side can include a texture that is different than the substrate application side.

In certain embodiments, the substrate can be a nonwoven (i.e. a natural or synthetic nonwoven including fibrous and nonfibrous nonwovens), a woven, a film (e.g. a formed film), a sponge (e.g. a natural and/or synthetic sponge), a polymeric netted mesh (i.e. a "scrim"), a batting, spunbond, spunlace, hydroentangled, carded, needlepunch, or any other suitable material.

Suitable formed films for use as a substrate in the home care article can include plastic formed films, such as polyolefins, including, for example, low density polyethylene (LDPE) films, hydroapertured polyethylene films with one or more openings such as apertures of from about 0.1 mm to about 3 mm, and combinations thereof. Many of such films are available from Tredegar, Inc.

When selecting formed films, some parameters to consider include: thickness, pattern, polymer stiffness, and permeability. Thickness can be measured by physical measurement of the thickness (like by using a caliper) or basis weight. In one embodiment, the thickness of the film substrate is from about 1.5 mm to about 5 mm. In another embodiment, the film substrate has a basis weight from about 10 g/m$^2$ to about 100 g/m$^2$. The pattern of the film substrate may also be important. For cleansing embodiments, a square or hex pattern gives better properties of appearance and cleansing ability.

Polymer stiffness of formed films affects texture and bending. When looking at polymer stiffness, $T_g$, glass transition temperature, is a good indicator. In one embodiment, a polymer used to form a film substrate has a $T_g$ of about −20° C. to about −125° C. Also, depending on other factors, like the desired consumption rate of the article, the permeability of a formed film can be important. Permeability is often measured as the rate of flux of a fluid through a substrate under a standard set of conditions. A test for determining water flux is below. In one embodiment, a film substrate has a pore open area of about 2% to about 20%.

The substrate can also be a nonwoven. A nonwoven typically has land regions (i.e. regions that do not allow water and/or the cleansing composition to pass through) and openings. In one embodiment, the nonwoven can provide sufficient air space between, for example, openings and land regions of the substrate and can help control permeability of the substrate. The nonwoven substrate can be fibrous or non-fibrous.

Suitable fibrous nonwovens for use as a substrate in a home care article can include a spunlaid hydroentangled 100% polypropylene (PP) available from Avgol Nonwovens, NC, USA; a carded, calendar bonded all bi-component polypropylene/polyethylene (PP/PE) fiber available from Fiberweb Inc., TN, USA; a spunbond, overbonded 100% PP, and a carded, through air bonded 30/30/40 PP/Bi-component PP-PE/Rayon.

An additional nonwoven suitable for use as a substrate herein includes batting fibers which can include fusible battings. Fusible battings may be fused, for example, by thermoplastic adhesives or via bicomponent fibers. For example, a nonwoven substrate can include a low loft all polyester batting available from Fairfield Processing, Danbury, Conn., USA; a low loft all polyester, ½ thickness (peeled) batting available from Fairfield Processing, Danbury, Conn., USA; a PROEF 12-334 polyester-bicomponent fiber blend batting available from Libeltex, Belgium; a PROEF 12-370 dual layer PET/copet bico and PP fibers available from Libeltex, Belgium; a bulk layer with standard PET/coPET bicotrilobal fibers available from Libeltex, Belgium; a dry web T30 SC batting, hollow PET+bico PET/PE fiber blend, air bonded available from Libeltex, Belgium; a PROEF 12-372 batting, coarse polyester, and PE/PET bico fibers available from Libeltex, Belgium; and a dry web T23W batting, coarse polyester and bico fiber mix available from Libeltex, Belgium.

Polymeric netted meshes or scrims can also be useful as a substrate for a home care article. Some examples can include those described in U.S. Pat. No. 4,636,419: In one embodiment, the substrate comprises a polypropylene scrim or a polyethylene scrim. In a further embodiment, the substrate comprises a low density polyethylene scrim.

A substrate may comprise a polymeric mesh sponge. Some suitable polymeric mesh sponges are described in European Patent Application No. EP 702550A1 published Mar. 27, 1996. Polymeric mesh sponges can comprise a plurality of plies of an extruded tubular netting mesh prepared from a strong flexible polymer, such as addition polymers of olefin monomers and polyamides of polycarboxylic acids.

In certain embodiments, a substrate can also be a composite material that includes, for example, one or more plies of the same or different materials such as nonwovens, wovens, films, sponges, scrims, battings, and the like superimposed physically, joined together continuously (e.g., laminated, etc.) in a discontinuous pattern, or by bonding at the external edges (or periphery) of the substrate and/or at discrete loci. The substrate can be a composite material comprising at least one formed film and at least one nonwoven where the substrate can be vacuum-formed. Such a suitable formed film composite material can include, for example, a vacuum-laminated composite formed film material that can be made or formed by combining a carded polypropylene nonwoven having a basis weight of 30 gm$^2$ with a formed film.

Additionally, as described above, a substrate can include one or more openings such that water, the composition, and/or suds, for example, can pass through the substrate. In one embodiment, where the permeable substrate is adjacent to the composition, the water passes through the water permeable substrate to interact with the cleansing composition. As the composition dissolves, it will then also pass through the substrate to be delivered to the target surface, like the skin.

In one embodiment, the permeability of the openings can be selected based on the dissolution half life of the cleansing composition and the desired reusability of the article. For example, when the dissolution half life of the cleansing composition is high, a higher level of permeability can be selected to counteract the high dissolution half life and provide a desirable consumption rate for the article. Alternatively, when the dissolution half life of the cleansing composition is low, the permeability of the one or more openings or can be lower and still provide a desirable consumption rate for the article. In varying embodiments, a substrate can include a permeability of about 1 opening/cm$^2$ or greater, about 10 openings/cm$^2$ or greater, about 100 openings/cm$^2$ or greater, about 500 openings/cm² or greater, about 1,000 openings/cm² or greater, about 1,500 openings/cm² or greater, or any combination thereof.

The openings can be apertured, nonapertured, or a combination thereof. For example, the one or more openings can include well-defined apertures such as microapertures or macroapertures, holes, perforations, cavities, raised or depressed fibrous and/or nonfibrous regions, gaps between regions, and the like that can enable, for example, water and/or the cleansing composition to pass through the substrate.

In one embodiment, a home care article comprises more than one substrate. In one embodiment, a home care article comprises more than one contact substrate. A combination of contact substrates may be used, for example, to give different properties to different sides of an article. Using FIG. 3B as an example, the first water insoluble substrate 26 may be a contact substrate which helps gripping and the second water insoluble substrate 28 may be a contact substrate on another portion of the article selected for its application properties. As another example, in one embodiment, the article has an exfoliating contact substrate on one side of the article and a soothing contact substrate on the other side.

A home care article may also comprise more than one substrate where one substrate comprises a contact substrate and another substrate a noncontact substrate. Using FIG. 3B as an example, the first and second water insoluble substrates 26, 28 would both be contact substrates, while the first and second substrates 22, 24 would be noncontact substrates. In one embodiment, a noncontact substrate is at least partially surrounded by at least one contact substrate. In another embodiment, two noncontact substrates are surrounded by two contact substrates. Additional contact and non-contact substrates may also surround other substrates and/or a composition.

A combination of substrates can be used to not only give different user experience properties, but it may also be used to give other desirable properties of an article, like appropriate consumption rate and suds profile. When combining substrates to form an article, one should consider the properties of the composition, in addition to the individual properties of the substrates, to come up with the article with the desired properties. For example, in one embodiment, a home care composition is surrounded by two noncontact substrates which are surrounded by two contact substrates. In a further embodiment, the two noncontact substrates are the same. In a further embodiment, the two contact substrates are the same.

Some examples of suitable substrates are included below.

B. Cleansing Composition

As noted above, a home care article comprises a substrate and a cleansing composition. In one embodiment, the home care composition is compliant as discussed above. The cleansing composition may have a compliance value 0.01-1.50 kg/mm.

In some embodiments, the cleansing composition will have a dissolution half life. In varying embodiments, the cleansing composition has a dissolution half life of about 1.0 min. to about 15 min.; about 1.1 min. to about 13 min.; from about 1.2 min. to about 12 min.; about 1.3 min. to about 11 min.; about 1.4 min. to about 8.0 min.; about 1.5 min. to about 5 min.; or any combination thereof.

The cleansing composition may be adjacent to one or more substrates. For example, the home care article can include a composition disposed between the one or more substrates. As shown in FIG. 3A, the composition 14 can be disposed within and adjacent to the water penetrable first substrate 12 such that the first substrate 12 can surround the cleansing composition 14. As described above, the substrate can activate and/or engage the composition.

The composition may be in the any suitable form. For example, the composition may be in the form of a bar, paste, gel, pellets, beads, or a combination thereof. Additionally, the composition may be of any shape desirable to a user. The composition of the present invention may be a hard surface cleansing composition, a hand dishwashing cleansing composition, or any other cleansing composition as known in the art.

In one preferred embodiment, the composition is a hard surface cleaning composition, the composition comprises from about 70% to about 99%, preferably from about 75% to about 95%, and more preferably from about 80% to about 95% by weight of the total composition, of water.

Alternatively, in another preferred embodiment, the composition is a hand dishwashing cleansing composition, the composition comprises from about 30% to about 95%, preferably from about 40% to about 80%, and more preferably from about 50% to about 75% by weight of the total composition, of water.

In the preferred embodiment wherein the composition is a hard surface cleansing composition, the composition has a pH from about 2 to about 14, preferably from about 2 to about 10, more preferably from about 2 to about 9.5, and even more preferably from about 2.1 to about 8, as is measured at 25° C. In the preferred embodiment wherein the composition is a hand dishwashing cleansing composition, the composition has a pH from about 3 to about 14, preferably from about 6 to about 13, most preferably from about 8 to about 11.

In one preferred embodiment, the composition has a water-like viscosity. By "water-like viscosity" it is meant herein a viscosity that is close to that of water. Preferably, the composition herein has a viscosity of up to about 50 cps, more preferably from about 0 cps to about 30 cps, yet more preferably from about 0 cps to about 20 cps, and most preferably from about 0 cps to about 10 cps at 60 rpm and 20° C., when measured with a Brookfield digital viscometer model DV II, with spindle 2.

In another preferred embodiment, the composition of the present invention is a thickened composition. Thus, the composition herein preferably has a viscosity of from about 50 cps to about 5000 cps, more preferably from about 50 cps to about 2000 cps, yet more preferably from about 50 cps to about 1000 cps, and most preferably from about 50 cps to about 500 cps at 20 $s^{-1}$ and 20° C., when measured with a Rheometer, model AR 1000 (Supplied by TA Instruments) with a 4 cm conic spindle in stainless steel, 2° angle (linear increment from 0.1 to 100 $sec^{-1}$ in maximum 8 minutes). Preferably, the thickened composition according to the embodiment is a shear-thinning composition. The thickened composition herein preferably comprises a thickener, more preferably a polysaccharide polymer thickener, still more preferably a gum-type polysaccharide polymer thickener, and most preferably a Xanthan gum thickener. In one preferred embodiment, the thickener may be micro fibril cellulose.

Incorporated and included herein, as if expressly written herein, are all ranges of numbers when written in a "from X to Y" or "from about X to about Y" format. It should be understood that every limit given throughout this specification will include every lower or higher limit, as the case may be, as if such lower or higher limit was expressly written herein. Every range given throughout this specification will include every narrower range that falls within such broader range, as if such narrower ranges were all expressly written herein.

Unless otherwise indicated, weight percentage is in reference to weight percentage of the liquid detergent composition. All temperatures, unless otherwise indicated are in Celsius.

Surfactant

Surfactants may be desired herein as they contribute to the cleaning performance of the cleansing compositions of the present invention. Suitable surfactants are selected from the group consisting of a nonionic surfactant or a mixture thereof; an anionic surfactant or a mixture thereof; an amphoteric surfactant or a mixture thereof; a zwitterionic surfactant or a mixture thereof; a cationic surfactant or a mixture thereof; and mixtures thereof.

In the preferred embodiment wherein the composition is a hard surface cleansing, composition, the composition comprises from about 1% to about 60%, preferably from about 5% to about 30%, and more preferably from about 10% to about 25% by weight of the total composition of a surfactant.

In the preferred embodiment wherein the composition is a hand dishwashing cleansing composition, the composition may comprise from about 5% to about 80%, preferably from about 10% to about 60%, more preferably from about 12% to about 45% by weight of the total composition of a surfactant. In preferred embodiments, the surfactant herein has an average branching of the alkyl chain(s) of more than about 10%, preferably more than about 20%, more preferably more than about 30%, and even more preferably more than about 40% by weight of the total surfactant.

Nonionic Surfactant

In one preferred embodiment, the cleansing composition comprises a nonionic surfactant. Suitable nonionic surfactants may be alkoxylated alcohol nonionic surfactants, which can be readily made by condensation processes which are well-known in the art. However, a great variety of such alkoxylated alcohols, especially ethoxylated and/or propoxylated alcohols, are commercially available. Surfactant catalogs are available which list a number of such surfactants, including nonionics.

Accordingly, preferred alkoxylated alcohols for use herein are nonionic surfactants according to the formula $R^1O(E)_e(P)_pH$ where $R^1$ is a hydrocarbon chain of from about 2 to about 24 carbon atoms, E is ethylene oxide, P is propylene oxide, and e and p which represent the average degree of, respectively ethoxylation and propoxylation, are of from about 0 to about 24 (with the sum of e+p being at least 1). Preferably, the hydrophobic moiety of the nonionic compound can be a primary or secondary, straight or branched alcohol having from about 8 to about 24 carbon atoms.

In some embodiments, preferred nonionic surfactants are the condensation products of ethylene oxide and/or propylene oxide with an alcohol having a straight or branched alkyl chain, having from about 6 to about 22 carbon atoms, preferably from about 9 to about 15 carbon atoms, wherein the degree of alkoxylation (ethoxylation and/or propoxylation) is from about 1 to about 25, preferably from about 2 to about 18, and more preferably from about 5 to about 12 moles of alkylene oxide per mole of alcohol. Particularly preferred are such surfactants containing from about 5 to about 12 moles of ethylene oxide per mole of alcohol. Such suitable nonionic surfactants are commercially available from Shell, for instance, under the trade name Neodol® or from BASF under the trade name Lutensol®.

Preferably, the nonionic surfactant is comprised in a typical amount of from about 2% to about 40%, preferably from about 3% to about 30% by weight of the cleansing composition, and preferably from about 3 to about 20% by weight of the total composition.

Also suitable are alkylpolyglycosides having the formula $R^3O(C_nH_{2n}O)_t(\text{glycosyl})_z$ (formula (III)), wherein $R^3$ of formula (III) is selected from the group consisting of an alkyl or a mixture thereof; an alkyl-phenyl or a mixture thereof; a hydroxyalkyl or a mixture thereof; a hydroxyalkylphenyl or a mixture thereof; and mixtures thereof, in which the alkyl group contains from about 10 to about 18, preferably from about 12 to about 14 carbon atoms; n of formula (III) is about 2 or about 3, preferably about 2; t of formula (III) is from about 0 to about 10, preferably about 0; and z of formula (III) is from about 1.3 to about 10, preferably from about 1.3 to about 3, most preferably from about 1.3 to about 2.7. The glycosyl is preferably derived from glucose. Also suitable are alkyl glycerol ether and sorbitan ester.

Also suitable is fatty acid amide surfactant having the formula (IV):

wherein $R^6$ of formula (IV) is an alkyl group containing from about 7 to about 21, preferably from about 9 to about 17, carbon atoms, and each $R^7$ of formula (IV) is selected from the group consisting of hydrogen; a $C_1$-$C_4$ alkyl or a mixture thereof; a $C_1$-$C_4$ hydroxyalkyl or a mixture thereof; and a —$(C_2H_4O)_yH$ or a mixture thereof, where y of formula (IV) varies from about 1 to about 3. Preferred amide can be a $C_8$-$C_{20}$ ammonia amide, a monoethanolamide, a diethanolamide, and an isopropanolamide.

Other preferred nonionic surfactants for use in the cleansing composition may be the mixture of nonyl ($C_9$), decyl ($C_{10}$) undecyl ($C_{11}$) alcohols modified with, on average, about 5 ethylene oxide (EO) units such as the commercially available Neodol 91-5® or the Neodol 91-8® that is modified with on average about 8 EO units. Also suitable are the longer alkyl chains ethoxylated nonionics such as $C_{12}$ or $C_{13}$ modified with 5 EO (Neodol 23-5®). Neodol® is a Shell tradename. Also suitable is the $C_{12}$ or $C_{14}$ alkyl chain with 7 EO, commercially available under the trade name Novel 1412-7® (Sasol) or the Lutensol A 7 N® (BASF).

Preferred branched nonionic surfactants are the Guerbet $C_{10}$ alcohol ethoxylates with 5 EO such as Ethylan 1005, Lutensol XP 50® and the Guerbet $C_{10}$ alcohol alkoxylated nonionics (modified with EO and PO (propylene oxide)) such as the commercially available Lutensol XL® series (X150, XL70, etc). Other branching also includes oxo branched nonionic surfactants such as the Lutensol ON 50® (5 EO) and Lutensol ON70® (7 EO). Other suitable branched nonionics are the ones derived from the isotridecyl alcohol and modified with ethylene oxide such as the Lutensol TO7® (7EO) from BASF and the Marlipal O 13/70® (7 EO) from Sasol. Also suitable are the ethoxylated fatty alcohols originating from the Fisher & Tropsch reaction conprising up to about 50% branching (about 40% methyl (mono or bi) about 10% cyclohexyl) such as those produced from the Safol® alcohols from Sasol; ethoxylated fatty alcohols originating from the oxo reaction wherein at least 50 wt % of the alcohol is $C_2$ isomer (methyl to pentyl) such as those produced from the Isalchem® alcohols or Lial® alcohols from Sasol; the ethoxylated fatty alcohols originating from the modified oxo reaction wherein at least about 15% by weight of the alcohol is $C_2$ isomer (methyl to pentyl) such as those produced from the Neodol® alcohols from Shell.

In one preferred embodiment, the weight ratio of total surfactant to nonionic surfactant is from about 2 to about 10, preferably from about 2 to about 7.5, more preferably from about 2 to about 6.

Anionic Surfactant

Suitable anionic surfactants for use in the cleansing composition can be a sulfate, a sulfosuccinate, a sulfoacetate, and/or a sulphonate; preferably an alkyl sulfate and/or an alkyl ethoxy sulfate; more preferably a combination of an alkyl sulfate and/or an alkyl ethoxy sulfate with a combined ethoxylation degree less than about 5, preferably less than about 3, more preferably less than about 2.

Sulphate or sulphonate surfactant is typically present at a level of at least about 5%, preferably from about 5% to about 40%, and more preferably from about 15% to about 30%, and even more preferably at about 15% to about 25% by weight of the cleansing composition.

Suitable sulphate or sulphonate surfactants for use in the cleansing composition include water-soluble salts or acids of $C_8$-$C_{14}$ alkyl or hydroxyalkyl, sulphate or sulphonates. Suitable counterions include hydrogen, alkali metal cation or ammonium or substituted ammonium, but preferably sodium. Where the hydrocarbyl chain is branched, it preferably comprises a $C_{1-4}$ alkyl branching unit. The average percentage branching of the sulphate or sulphonate surfactant is preferably greater than about 30%, more preferably from about 35% to about 80%, and most preferably from about 40% to about 60% of the total hydrocarbyl chain. One particularly suitable linear alkyl sulphonate includes $C_8$ sulphonate like Witconate NAS 8® commercially available from Witco.

The sulphate or sulphonate surfactants may be selected from a $C_{11}$-$C_{18}$ alkyl benzene sulphonate (LAS), a $C_8$-$C_{20}$ primary, a branched-chain and random alkyl sulphate (AS); a $C_{10}$-$C_{18}$ secondary (2,3) alkyl sulphate; a $C_{10}$-$C_{18}$ alkyl alkoxy sulphate ($AE_xS$) wherein preferably x is from 1-30; a $C_{10}$-$C_{18}$ alkyl alkoxy carboxylate preferably comprising about 1-5 ethoxy units; a mid-chain branched alkyl sulphate as discussed in U.S. Pat. No. 6,020,303 and U.S. Pat. No. 6,060,443; a mid-chain branched alkyl alkoxy sulphate as discussed in U.S. Pat. No. 6,008,181 and U.S. Pat. No. 6,020,303; a modified alkylbenzene sulphonate (MLAS) as discussed in WO 99/05243, WO 99/05242, WO 99/05244, WO 99/05082, WO 99/05084, WO 99/05241, WO 99/07656, WO 00/23549, and WO 00/23548; a methyl ester sulphonate (MES); and an alpha-olefin sulphonate (AOS).

The paraffin sulphonate may be monosulphonate or disulphonate and usually are mixtures thereof, obtained by sulphonating a paraffin of about 10 to about 20 carbon atoms. Preferred sulphonates are those of $C_{12-18}$ carbon atoms chains and more preferably they are $C_{14-17}$ chains. Paraffin sulphonates that have the sulphonate group(s) distributed along the paraffin chain are described in U.S. Pat. Nos. 2,503,280; 2,507,088; 3,260,744; and 3,372,188.

Also suitable are the alkyl glyceryl sulphonate surfactant and/or alkyl glyceryl sulphate surfactant described in the Procter & Gamble patent application WO06/014740: A mixture of oligomeric alkyl glyceryl sulphonate and/or sulfate surfactant selected from a dimmer or a mixture thereof; a trimer or a mixture thereof; a tetramer or a mixture thereof; a pentamer or a mixture thereof; a hexamer or a mixture thereof; a heptamer or a mixture thereof; and mixtures thereof; wherein the alkyl glyceryl sulphonate and/or sulfate surfactant mixture comprises from about 0% to about 60% by weight of the monomers.

Other suitable anionic surfactants are alkyl, preferably dialkyl sulfosuccinate and/or sulfoacetate. The dialkyl sulfosuccinate may be a $C_{6-15}$ linear or branched dialkyl sulfosuccinate. The alkyl moiety may be symmetrical (i.e., the same alkyl moieties) or asymmetrical (i.e., different alkyl moieties). Preferably, the alkyl moiety is symmetrical.

Most common branched anionic alkyl ether sulphates are obtained via sulfation of a mixture of the branched alcohols and the branched alcohol ethoxylates. Also suitable are the sulfated fatty alcohols originating from the Fischer & Tropsh reaction comprising up to about 50% branching (about 40% methyl (mono or bi) about 10% cyclohexyl) such as those produced from the safol alcohols from Sasol; sulfated fatty alcohols originating from the oxo reaction wherein at least about 50% by weight of the alcohol is $C_2$ isomer (methyl to pentyl) such as those produced from the Isalchem® alcohols or Lial® alcohols from Sasol; the sulfated fatty alcohols originating from the modified oxo reaction wherein at least about 15% by weight of the alcohol is $C_2$ isomer (methyl to pentyl) such as those produced from the Neodol® alcohols from Shell.

Zwitterionic Surfactant and Amphoteric Surfactant

The zwitterionic and amphoteric surfactants for use in the cleansing composition can be comprised at a level of from about 0.01% to about 20%, preferably from about 0.2% to about 15%, more preferably from about 0.5% to about 10% by weight of the cleansing composition.

Suitable zwitterionic surfactant in the preferred embodiment wherein contains both basic and acidic groups which form an inner salt giving both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylate and sulphonate, although other groups like sulfate, phosphonate, and the like can be used.

The cleansing compositions may preferably further comprise an amine oxide and/or a betaine. Most preferred amine oxides are coconut dimethyl amine oxide or coconut amido propyl dimethyl amine oxide. Amine oxide may have a linear or mid-branched alkyl moiety. Typical linear amine oxides include water-soluble amine oxide containing one $R^4$ $C_{8-18}$ alkyl moiety and 2 $R^5$ and $R^8$ moieties selected from the group consisting of a $C_{1-3}$ alkyl group and a mixtures thereof; and a $C_{1-3}$ hydroxyalkyl group and a mixture thereof. Preferably amine oxide is characterized by the formula $R^4$—$N(R^5)(R^8)$ →O wherein $R^4$ is a $C_{8-18}$ alkyl and $R^5$ and $R^8$ are selected from the group consisting of a methyl; an ethyl; a propyl; an isopropyl; a 2-hydroxethyl; a 2-hydroxypropyl; and a 3-hydroxypropyl. The linear amine oxide surfactant, in particular, may include a linear $C_{10}$-$C_{18}$ alkyl dimethyl amine oxide and a linear $C_8$-$C_{12}$ alkoxy ethyl dihydroxy ethyl amine oxide. Preferred amine oxides, include linear $C_{10}$, linear $C_{10}$-$C_{12}$, and linear $C_{12}$-$C_{14}$ alkyl dimethyl amine oxides.

As used herein "mid-branched" means that the amine oxide has one alkyl moiety having $n_1$ carbon atoms with one alkyl branch on the alkyl moiety having $n_2$ carbon atoms. The alkyl branch is located on the α carbon from the nitrogen on the alkyl moiety. This type of branching for the amine oxide is also known in the art as an internal amine oxide. The total sum of $n_1$ and $n_2$ is from about 10 to about 24 carbon atoms, preferably from about 12 to about 20, and more preferably from about 10 to about 16. The number of carbon atoms for the one alkyl moiety ($n_1$) should be approximately the same number of carbon atoms as the one alkyl branch ($n_2$) such that the one alkyl moiety and the one alkyl branch are symmetric. As used herein, "symmetric" means that $|n_1-n_2|$ is less than or equal to about 5, preferably about 4, most preferably from about 0 to about 4 carbon atoms in at least about 50 wt %, more preferably at least about 75 wt % to about 100 wt % of the mid-branched amine oxide for use herein.

The amine oxide further comprises two moieties, independently selected from a $C_{1-3}$ alkyl; a $C_{1-3}$ hydroxyalkyl group; or a polyethylene oxide group containing an average of from about 1 to about 3 ethylene oxide groups. Preferably the two moieties are selected from a $C_{1-3}$ alkyl, more preferably both are selected as a $C_1$ alkyl.

Other suitable surfactants include a betaine such an alkyl betaine, an alkylamidobetaine, an amidazoliniumbetaine, a sulfobetaine (INCI Sultaines), as well as a phosphobetaine, and preferably meets formula I:

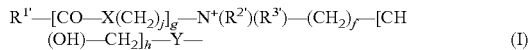

wherein
$R^{1'}$ is a saturated or unsaturated $C_{6-22}$ alkyl residue, preferably a $C_{8-18}$ alkyl residue, in particular a saturated $C_{10-16}$ alkyl residue, for example a saturated $C_{12-14}$ alkyl residue;
X is NH, $NR^{4'}$ with $C_{1-4}$ alkyl residue $R^{4'}$, O or S,
j is a number from about 1 to about 10, preferably from about 2 to about 5, in particular about 3,
g is about 0 or about 1, preferably about 1,
$R^{2'}$, $R^{3'}$ are independently a $C_{1-4}$ alkyl residue, potentially hydroxy substituted by such as a hydroxyethyl, preferably by a methyl.
f is a number from about 1 to about 4, in particular about 1, 2 or 3,
h is about 0 or 1, and
Y is selected from $COO$, $SO_3$, $OPO(OR^{5'})O$ or $P(O)(OR^{5'})O$, whereby $R^{5'}$ is a hydrogen atom H or a $C_{1-4}$ alkyl residue.

Preferred betaines are the alkyl betaine of the formula ($I_a$), the alkyl amido betaine of the formula ($I_b$), the sulfo betaine of the formula ($I_c$), and the Amido sulfobetaine of the formula ($I_d$);

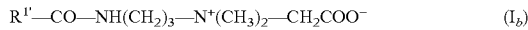

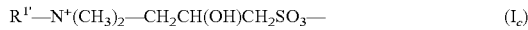

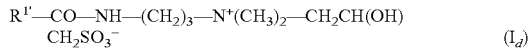

in which $R^{1'}$ has the same meaning as in formula I. Particularly preferred betaines are the carbobetaine, wherein $Y^-$ is $[COO^-]$, in particular the carbobetaine of formula ($I_a$) and ($I_b$), more preferred are the alkylamidobetaine of the formula ($I_b$).

Examples of suitable betaines and sulfobetaines are the following (designated in accordance with INCI): almondamidopropyl of betaine, apricotamidopropyl betaine, avocadamidopropyl of betaine, babassuamidopropyl of betaine, behenamidopropyl betaine, behenyl of betaine, betaine, canolamidopropyl betaine, capryl/capramidopropyl betaine, carnitine, cetyl of betaine, cocamidoethyl of betaine, cocamidopropyl betaine, cocamidopropyl hydroxysultaine, coco betaine, coco hydroxysultaine, coco/oleamidopropyl betaine, coco sultaine, decyl of betaine, dihydroxyethyl oleyl glycinate, dihydroxyethyl soy glycinate, dihydroxyethyl stearyl glycinate, dihydroxyethyl tallow glycinate, dimethicone propyl of PG-betaine, drucamidopropyl hydroxysultaine, hydrogenated tallow of betaine, isostearamidopropyl betaine, lauramidopropyl betaine, lauryl of betaine, lauryl hydroxysultaine, lauryl sultaine, milk amidopropyl betaine, milkamidopropyl of betaine, myristamidopropyl betaine, myristyl of betaine, oleamidopropyl betaine, oleamidopropyl hydroxysultaine, oleyl of betaine, olivamidopropyl of betaine, palmamidopropyl betaine, palmitamidopropyl betaine, palmitoyl carnitine, palm kernel amidopropyl betaine, polytetrafluoroethylene acetoxypropyl of betaine, ricinoleamidopropyl betaine, sesamidopropyl betaine, soyamidopropyl betaine, stearamidopropyl betaine, stearyl of betaine, tallowamidopropyl betaine, tallowamidopropyl hydroxysultaine, tallow of betaine, tallow dihydroxyethyl of betaine, undecylenamidopropyl betaine and wheat germ amidopropyl betaine. Preferred betaine is for example cocoamidopropyl betaine.

For example coconut dimethyl betaine is commercially available from Seppic under the trade name of Amonyl 265®. Lauryl betaine is commercially available from Albright & Wilson under the trade name Empigen BB/L®. A further example of betaine is lauryl-imino-dipropionate commercially available from Rhodia under the trade name Mirataine H2C-HA®.

One particularly preferred zwitterionic surfactants for use in the preferred embodiment wherein the composition is a hard surface cleaning composition is the sulfobetaine surfactant, because it delivers optimum soap scum cleaning benefits.

Examples of particularly suitable sulfobetaine surfactants include tallow bis(hydroxyethyl) sulphobetaine and cocoamido propyl hydroxy sulphobetaine which are commercially available from Rhodia and Witco, under the trade name of Mirataine CBS® and Rewoteric AM CAS15® respectively.

Cationic Surfactant

In one preferred embodiment, the cleansing composition can comprise a cationic surfactant present in an effective amount, more preferably from about 0.1% to about 20%, by weight of the cleansing composition. Suitable cationic surfactant is quaternary ammonium surfactant. Suitable quaternary ammonium surfactant is selected from the group consisting of a mono $C_6$-$C_{16}$, preferably a $C_6$-$C_{10}$ N-alkyl or an alkenyl ammonium surfactant or a mixture thereof, wherein the remaining N positions are substituted by a methyl, a hydroxyethyl or a hydroxypropyl group. Another preferred cationic surfactant is a $C_6$-$C_{18}$ alkyl or alkenyl ester of a quaternary ammonium alcohol, such as quaternary chlorine ester. More preferably, the cationic surfactant has formula (V):

wherein $R^9$ of formula (V) is a $C_8$-$C_{18}$ hydrocarbyl or a mixture thereof, preferably, a $C_{8-14}$ alkyl, more preferably, a $C_8$, $C_{10}$ or $C_{12}$ alkyl; and Z of formula (V) is an anion, preferably, a chloride or a bromide.

Optional Ingredients

The cleansing composition according to the present invention may comprise a variety of optional ingredients, depending on the technical benefit aimed for and the surfaces treated.

Suitable optional ingredients for use herein include an alkaline material or a mixture thereof; an inorganic or organic acid and salt thereof or a mixture thereof; a buffering agent or a mixture thereof; a surface modifying polymer or a mixture thereof; a cleaning polymer or a mixture thereof; a peroxygen bleach or a mixture thereof; a radical scavenger or a mixture thereof; a chelating agent or a mixture thereof; a perfume or a mixture thereof; a dye or a mixture thereof; a hydrotrope or a mixture thereof; a polymeric suds stabilizer or a mixture thereof; a diamine or a mixture thereof; and mixtures thereof.

Solvent

Solvents are generally used to ensure preferred product quality for dissolution, thickness and aesthetics and to ensure better processing. The cleansing composition of the present invention may further comprise a solvent or a mixture thereof, as an optional ingredient. Typically, in the preferred embodiment wherein the composition is a hard surface cleaning composition, the composition may comprise from about 0.1% to about 10%, preferably from about 0.5% to about 5%, and more preferably from about 1% to about 3% by weight of the total composition of a solvent or a mixture thereof. In the preferred embodiment wherein the composition is a hand dishwashing detergent composition, the composition contains from about 0.01% to about 20%, preferably from about 0.5% to about 20%, more preferably from about 1% to about 10% by weight of a solvent.

Suitable solvents herein include $C_1$-$C_5$ alcohols according to the formula $R^{10}$—OH wherein $R^{10}$ is a saturated alkyl group of from about 1 to about 5 carbon atoms, preferably from about 2 to about 4. Suitable alcohols are ethanol, propanol, isopropanol or mixtures thereof. Other suitable alcohols are alkoxylated $C_{1-8}$ alcohols according to the formula $R^{11}$-$(A_q)$-OH wherein $R^{11}$ is a alkyl group of from about 1 to about 8 carbon atoms, preferably from about 3 to about 6, and wherein A is an alkoxy group, preferably propoxy and/or ethoxy, and q is an integer of from 1 to 5, preferably from 1 to 2. Suitable alcohols are butoxy propoxy propanol (n-BPP), butoxy propanol (n-BP), butoxyethanol, or mixtures thereof. Suitable alkoxylated aromatic alcohols to be used herein are those according to the formula $R^{12}$—$(B)_r$—OH wherein $R^{12}$ is an alkyl substituted or non-alkyl substituted aryl group of from about 1 to about 20 carbon atoms, preferably from about 2 to about 15, and more preferably from about 2 to about 10, wherein B is an alkoxy group, preferably a butoxy, propoxy and/or ethoxy, and r is an integer of from 1 to 5, preferably from 1 to 2. A suitable aromatic alcohol to be used herein is benzyl alcohol. Suitable alkoxylated aromatic alcohol is benzylethanol and or benzylpropanol. Other suitable solvent includes butyl diglycolether, benzylalcohol, propoxypropoxypropanol (EP 0 859 044) ether and diether, glycol, alkoxylated glycol, $C_6$-$C_{16}$ glycol ether, alkoxylated aromatic alcohol, aromatic alcohol, aliphatic branched alcohol, alkoxylated aliphatic branched alcohol, alkoxylated linear $C_1$-$C_5$ alcohol, linear $C_1$-$C_5$ alcohol, amine, $C_8$-$C_{14}$ alkyl and cycloalkyl hydrocarbon and halohydrocarbon, and mixtures thereof.

Perfume

The cleansing composition of the present invention may comprise a perfume ingredient, or mixtures thereof, in amount up to about 5.0% by weight of the total composition, preferably in amount of about 0.1% to about 1.5%. Suitable perfume compounds and compositions for use herein are for example those described in EP-A-0 957 156 under the paragraph entitled "Perfume", on page 13.

Dye

The cleansing composition according to the present invention may be colored. Accordingly, it may comprise a dye or a mixture thereof. Suitable dyes for use herein are acid-stable dyes. By "acid-stable", it is meant herein a compound which is chemically and physically stable in the acidic environment of the composition herein.

pH Adjustment Agent

Alkaline Material

Preferably, an alkaline material may be present to trim the pH and/or maintain the pH of the composition according to the present invention. The amount of alkaline material is from about 0.001% to about 20%, preferably from about 0.01% to about 10%, and more preferably from about 0.05% to about 3% by weight of the composition.

Examples of the alkaline material are sodium hydroxide, potassium hydroxide and/or lithium hydroxide, and/or the alkali metal oxide, such as sodium and/or potassium oxide, or mixtures thereof. Preferably, the source of alkalinity is sodium hydroxide or potassium hydroxide, preferably sodium hydroxide.

Acid

The cleansing composition of the present invention may comprise an acid. Any acid known to those skilled in the art may be used herein. Typically the composition herein may comprise up to about 20%, preferably from about 0.1% to about 10%, more preferably from about 0.1% to about 5%, even more preferably from about 0.1% to about 3%, by weight of the total composition of an acid.

Suitable acids are selected from the group consisting of a mono- and poly-carboxylic acid or a mixture thereof; a percarboxylic acid or a mixture thereof; a substituted carboxylic acid or a mixture thereof; and mixtures thereof. Carboxylic acids useful herein include $C_{1-5}$ linear or at least about 3 carbon containing cyclic acids. The linear or cyclic carbon-containing chain of the carboxylic acid may be substituted with a substituent group selected from the group consisting of hydroxyl, ester, ether, aliphatic groups having from about 1 to about 6, more preferably from about 1 to about 4 carbon atoms, and mixtures thereof.

Suitable mono- and poly-carboxylic acids are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and mixtures thereof.

Suitable percarboxylic acids are selected from the group consisting of peracetic acid, percarbonic acid, perboric acid, and mixtures thereof.

Suitable substituted carboxylic acids are selected from the group consisting of an amino acid or a mixture thereof; a halogenated carboxylic acid or a mixture thereof; and mixtures thereof.

Preferred acids for use herein are selected from the group consisting of lactic acid, citric acid, and ascorbic acid and mixtures thereof. More preferred acids for use herein are selected from the group consisting of lactic acid and citric acid and mixtures thereof. An even more preferred acid for use herein is lactic acid.

Suitable acids are commercially available from JBL, T&L, or Sigma. Lactic acid is commercially available from Sigma and Purac.

Salt

In a preferred embodiment, the cleansing composition of the present invention also comprises other salts as the pH buffer. Salts are generally present at an active level of from about 0.01% to about 5%, preferably from about 0.015% to about 3%, more preferably from about 0.025% to about 2.0%, by weight of the composition.

When salts are included, the ions can be selected from magnesium, sodium, potassium, calcium, and/or magnesium, and preferably from sodium and magnesium, and are added as a hydroxide, chloride, acetate, sulphate, formate, oxide or nitrate salt to the composition of the present invention.

Diamine

In another preferred embodiment, the cleansing composition of the present invention comprises a diamine or a mixture thereof as the pH buffer. The composition will preferably contain from about 0% to about 15%, preferably from about 0.1% to about 15%, preferably from about 0.2% to about 10%, more preferably from about 0.25% to about 6%, more preferably from about 0.5% to about 1.5% by weight of the total composition of at least one diamine.

Preferred organic diamines are those in which $pK_1$ and $pK_2$ are in the range of from about 8.0 to about 11.5, preferably in the range of from about 8.4 to about 11, even more preferably from about 8.6 to about 10.75. Preferred materials include 1,3-bis(methylamine) cyclohexane (pKa=from about 10 to about 10.5), 1,3-propane diamine ($pK_1$=10.5; $pK_2$=8.8), 1,6-hexane diamine ($pK_1$=11; $pK_2$=10), 1,3-pentane diamine (DYTEK EP®) ($pK_1$=10.5; $pK_2$=8.9), 2-methyl-1,5-pentane diamine (DYTEK A®) ($pK_1$=11.2; $pK_2$=10.0). Other preferred materials include primary/primary diamines with alkylene spacers ranging from $C_4$ to $C_8$. In general, it is believed that primary diamines are preferred over secondary and tertiary diamines. pKa is used 0.15 herein in the same manner as is commonly known to people skilled in the art of chemistry: in an all-aqueous solution at 25° C. and for an ionic strength between about 0.1 to about 0.5 M, values. Reference can be obtained from literature, such as from "Critical Stability Constants: Volume 2, Amines" by Smith and Martel, Plenum Press, NY and London, 1975.

Chelant

It has been found that the addition of a chelant, in the cleansing composition of the present invention provides an unexpected improvement in terms of its cleaning capability. In a preferred embodiment, the composition of the present invention may comprise a chelant at a level of from about 0.1% to about 20%, preferably from about 0.2% to about 5%, more preferably from about 0.2% to about 3% by weight of total composition.

Suitable chelants can be selected from the group consisting of an amino carboxylate or a mixture thereof; an amino phosphonate or a mixture thereof; a polyfunctionally-substituted aromatic chelant or a mixture thereof; and mixtures thereof.

Preferred chelants for use herein are the amino acid based chelants, and preferably glutamic-N,N-diacetic acid (GLDA) and derivatives, and/or phosphonate based chelants, and preferably diethylenetriamine pentamethylphosphonic acid. GLDA (salts and derivatives thereof) is especially preferred according to the invention, with the tetrasodium salt thereof being especially preferred.

Also preferred are amino carboxylates including ethylenediaminetetra-acetate, N-hydroxyethylethylenediaminetriacetate, nitrilo-triacetate, ethylenediamine tetrapro-prionate, triethylenetetraaminehexacetate, diethylenetriaminepentaacetate, ethanoldi-glycine; and alkali metal, ammonium, and substituted ammonium salts thereof; and mixtures thereof; as well as MGDA (methylglycine-diacetic acid), and salts and derivatives thereof.

Other chelants include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least about two carboxyl groups which are in each case separated from one another by, preferably, no more than about two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid.

Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulphonates.

Further suitable polycarboxylates chelants for use herein include acetic acid, succinic acid, formic acid; all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

Amino phosphonates are also suitable for use as chelant and include ethylenediaminetetrakis (methylenephosphonates) as DEQUEST. Preferably, these amino phosphonates do not contain alkyl or alkenyl groups with more than about 6 carbon atoms.

Polyfunctionally-substituted aromatic chelants are also useful in the composition herein, such as described in U.S. Pat. No. 3,812,044. Preferred compounds of this type in acid form are dihydroxydisulfobenzenes such as 1,2-dihydroxy-3,5-disulfobenzene.

Hydrotrope

The cleansing composition of the present invention may optionally comprise a hydrotrope in an effective amount so that the composition is appropriately compatible in water. The composition of the present invention typically comprises from about 0% to about 15% by weight of the total composition of a hydrotropic, or mixtures thereof, preferably from about 1% to about 10%, most preferably from about 3% to about 6%. Suitable hydrotropes for use herein include anionic-type hydrotropes, particularly sodium, potassium, and ammonium xylene sulphonate, sodium, potassium and ammonium toluene sulphonate, sodium potassium and ammonium cumene sulphonate, and mixtures thereof, and related compounds, as disclosed in U.S. Pat. No. 3,915,903.

Polymeric Suds Stabilizer

The cleansing composition of the present invention may optionally contain a polymeric suds stabilizer. These polymeric suds stabilizers provide extended suds volume and suds duration of the composition. The composition preferably contains from about 0.01% to about 15%, preferably from about 0.05% to about 10%, more preferably from about 0.1% to about 5%, by weight of the total composition of the polymeric suds booster/stabilizer.

These polymeric suds stabilizers may be selected from homopolymers of a (N,N-dialkylamino) alkyl ester and a (N,N-dialkylamino) alkyl acrylate ester. The weight average molecular weight of the polymeric suds booster, determined via conventional gel permeation chromatography, is from about 1,000 to about 2,000,000, preferably from about 5,000 to about 1,000,000, more preferably from about 10,000 to about 750,000, more preferably from about 20,000 to about 500,000, even more preferably from about 35,000 to about 200,000. The polymeric suds stabilizer can optionally be present in the form of a salt, either an inorganic or organic salt, for example the citrate, sulphate, or nitrate salt of (N,N-dimethylamino)alkyl acrylate ester.

One preferred polymeric suds stabilizer is (N,N-dimethylamino)alkyl acrylate ester, namely the acrylate ester represented by the formula (VII):

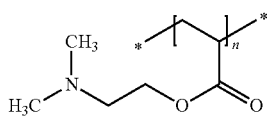

(VII)

Other preferred suds boosting polymers are copolymers of hydroxypropylacrylate/dimethyl aminoethylmethacrylate (copolymer of HPA/DMAM), represented by the formulae VIII and IX

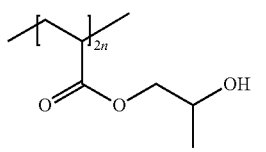

(VIII)

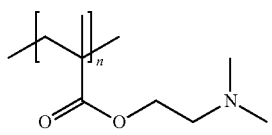

(IX)

Another preferred class of polymeric suds booster polymers are hydrophobically modified cellulosic polymers having a weight average molecular weight ($M_w$) below about 45,000; preferably between about 10,000 and about 40,000; more preferably between about 13,000 and about 25,000. The hydrophobically modified cellulosic polymers include water soluble cellulose ether derivatives, such as nonionic and cationic cellulose derivatives. Preferred cellulose derivatives include methylcellulose, hydroxypropyl methylcellulose, hydroxyethyl methylcellulose, and mixtures thereof.

III. Methods of Manufacture

Home care articles can be manufactured by adding the cleansing composition to an appropriate substrate via a conventional method which may include, but is not limited to, spraying, slot coating, molding such as rotary molding, extrusion, injection, feeding from a hopper and cutting such as by wire cutting, and roll transfer (e.g., pressure roll). A second substrate can then be placed on the first substrate over at least part of the cleansing composition. The home care articles may also be manufactured by a hot melt method as discussed in the application titled "Personal Cleansing Articles Comprising Substrates and Cleansing Compositions and Methods of Making the Same" filed on even date herewith and is incorporated herein by reference. The substrates can be sealed together by a conventional sealing method which may include, but is not limited to, heat, pressure, glue, ultrasound, etc. Optional manufacturing steps may include calendaring to flatten the article as well as drying.

IV. Methods of Use

A method of cleansing the target surface with a cleansing article can include wetting with water a reusable cleansing article and contacting the target surface with the wetted cleansing article.

The home care articles can be intended to be wetted with water prior to use. The home care article can be wetted, for example, by immersion in water or by placing the home cleansing article under a stream of water. In one embodiment, suds can be generated from the home care article by mechanically agitating and/or deforming the cleansing article either prior to or during contact of the cleansing article with the target surface. The resulting suds can be useful for cleansing the target surface.

V. Procedures

The home care article, compositions, and substrates can include and/or exhibit specific physical properties as defined by the water flux rate test, the consumption rate test, the substrate and article tensile test, the dissolution rate test, an oscillatory rheology test, and/or the compliance test, which are described below.

A. Water Flux Rate Test

The water flux rate test can measure water permeability of a substrate. Without intending to be limited by theory, water permeability can be a principal determinant of surfactant longevity in a sudsing substrate that is used in a presence of water, especially running water. When a surfactant can be present, it can be desirable for the surfactant to suds quickly and profusely, yet be fully depleted at an intended time to signal disposability of a used substrate. If water flux rate is too low, e.g. zero or near zero, insufficient wetting of the surfactant contained in the substrate can cause suds to start too slowly. On the other hand, if water flux rate is too high, surfactant can be too readily flushed from the substrate, and the composition will not last long enough.

To measure the water flux rate, with tape or rubber bands, affix a substrate to the bottom of a plastic funnel with the following measurements: a 24 mm inner diameter (i.d.) at an exit, a 145 mm i.d. at the top, 135 mm height (from the top to an onset of a neck), a 20 mm length neck, and a total volume of about 600 mL. Apply sufficient tension to the substrate to ensure the substrate is completely flat, and no more. Affix tape and rubber bands as close as possible to the exit of the funnel to keep backflow from occurring under water pressure. Next, clamp the funnel in a ring stand over a sink. Measure out 600 mL of water at room temperature in a graduated cylinder. Then, with one hand blocking the funnel exit, pushing against the test substrate, quickly pour the water into the funnel. Once the funnel is completely filled, remove the hand and measure drainage time for the water to evacuate the funnel to a nearest tenth of a second. Stop timing when the water reaches a junction of the neck and a sloped portion of the funnel. Repeat this process 5 times per test substrate and average the measurements for each substrate.

Substrates which exhibit long drainage times (about 10 minutes or longer) can be tested by weighing the water drained in a set time period (e.g. 5 minutes) with a funnel full of water and then algebraically determining the flux time for 600 mL of water. Next, measure the water flux rate in the opposite substrate direction (unless the substrate is the same in both directions), and average both results. For substrates with high surface tension against water and small pores (i.e., flow is observed to increase significantly with small amount of surfactant added), add a small but sufficient amount of wetting agent to the water (e.g., Dawn®™ dish liquid), to at least a critical micelle concentration, so that water flows through the substrate unimpeded by wetting forces prior to the test. The water flux rate is expressed in $cm^3/cm^2/s$ according to the following equation: Water flux rate=(600 g water)×(1 $cm^3$/g)/((1.2 $cm)^2$×(average time in seconds)).

B. Consumption Rate Test

To measure the Consumption Rate of a home care article or composition, use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (µS/cm) and heat in a reservoir beaker to 45° C. Maintain the water supply at the target temperature within 1 degree for the test duration. Add 200.0 gm water from the reservoir to the housing. Weigh an article or composition to obtain the initial weight, and add the article or composition to the housing. Seal the housing with its accompanying watertight lid and place the sealed housing onto the rotary tumbler for exactly 3 minutes. Remove the housing, remove the housing lid, and retrieve the article or composition. Stir the remaining water in the housing for a few seconds and measure its conductivity and temperature using a Mettler Toledo Seven multimeter with InLab 740 probe or equivalent. Dry the article or composition surface by pressing, not rubbing, using paper towels with light hand pressure for about 30 seconds, until it is dry to the touch and transfers no more visible water to a dry paper towel using the same pressure at any point on its surface or edges. If the article or composition transfers partially dissolved or dissolving components in addition to liquid water, for example if the composition is a conventional bar soap it may transfer paste-like material, the transferred components are to be removed and the article or composition is considered dry when visible transfer is no longer evident. Weigh the article or composition.

Empty and rinse the housing in hot tap water and dry it to complete 1 cycle. Repeat the cycle with the same article 4 more times for a total of 5 cycles. Measure the conductivity of the water reservoir at 30° C., 35° C., 40° C., and 45° C. Using a new article of the same composition, prepare a 0.1% solution by removing 1.00 grams of its dissolvable chemical composition and adding it to 99.00 grams of water from the reservoir. Dissolve the chemical composition completely, using agitation and heat as necessary. Measure conductivity of the 1% solution at the same 4 temperatures. Prepare a 2% solution in the same way (2.00 grams composition in 98.00 grams water), and measure its conductivity at the same 4 temperatures. Regress the conductivity vs. temperature results for each solution (0%, 1%, and 2%) and obtain the algebraic expressions for each.

For each conductivity-temperature datum for the water in the housing obtained during the each cycle, calculate the regressed conductivity for the 0%, 1% and 2% solutions at the temperature measured by the InLab 470 probe for each cycle. Execute a second set of linear regressions for each temperature obtained in the cycles using the solution concentrations (0%, 1% and 2%) as the y (output) and the regressed conductivity values as x (input). Use this second regression at each temperature obtained in each cycle with its paired conductivity value obtained as the input value for x to obtain y, which is the amount of solids of the article dissolved for each cycle. Add the dissolved solids for the 5 cycles and divide by 5 to obtain the Average Dissolved Solids. Multiply the value by 1.67 to obtain the consumption rate of the article which is based on the relationship between this method and consumption during use of articles in an average ad lib shower by consumers.

C. Substrate and Article Tensile Test

To measure the rigidity of a substrate and/or article, use a Texture Analyzer TA-XT2i (Texture Technologies Corp, NY, USA) tensile tester equipped with at least 5 kg load cell and adjustable upper and lower grips at ambient conditions. Adjust a gauge length of an instrument (grip to grip closest distance) to 50 mm. Cut 1 inch wide, long strips of the home care article or water insoluble substrate using a precision cutter in a machine direction (MD). (Note: Properties of an article can be measured by separating the cleansing composition from the substrates of the article by physical means and cutting 1 inch wide strips of the home care article with the cleansing composition removed.) If the strips are too short, adjust the gauge length of the instrument to accommodate the strips of the substrate, since the results are expressed in strain. Additionally, if the strips are too narrow, evaluate by normalizing results obtained to a 1 inch width arithmetically.

Affix the strips to grips in the instrument and program the instrument in tensile mode to pull at a rate of 5 trim/second and measure grams-force, using a 2.5 gram trigger to commence recording, for 20 seconds (100 mm). Next, record force at 10% strain in grams (5 mm) and divide the recorded force by 25.4 mm to express a stiffness value in units of grams per mm width (g/mm). Record peak force (grams) and divide the recorded peak force by width to generate the ultimate tensile strength in g/mm width of the article or substrate. For materials which exceed the capacity of a load cell, reduce the width of the strips or increase the load cell capacity to measure the stiffness and ultimate tensile strength.

D. Dissolution Rate Test

Obtain a straight walled glass beaker having an inside diameter (i.d.) of 63 mm and an inside height of 87 mm, (e.g. Pyrex 250 ml (No. 1000) which are widely available). Pour 150 grams of distilled water at ambient temperature (75° F.) into the beaker and add a Teflon® coated magnetic stir bar to the beaker. (Note: The stir bar can be nominally 1.5 inches long×5/16 inches diameter, octagonally shaped as viewed from the end, and can have a 1/16 in. wide molded pivot ring around its center where the diameter can be about 0.35 in.) Examples of a suitable stir bar can include Spinbar magnetic stir bars available from Sigma Aldrich Corp. worldwide including Milwaukee, Wis., USA and at www.sigmaaldrich.com.

Measure and record the water conductivity of the water using a conductivity meter, e.g., a Mettler-Toledo SevenMulti meter with InLab740 probe. (Note: The conductivity of the water should be about 2 microSemens/cm (uS/cm) or less to indicate a low level of dissolved solids present.) Remove the conductivity probe from the water and place the beaker onto a digitally controlled laboratory stirrer, for example Ika® Werke RET Control-visc available, e.g., from DivTech Equipment Co, Cincinnati, Ohio, USA. Center the beaker on the stirrer and turn the stirrer on to obtain a constant rotation speed of 500 rpm to establish a vortex in the water which measures about 3 cm in depth from highest point of water at the beaker edge to the lowest point of air at the vortex center. Observe the vortex from above to ensure the beaker is centered and the magnetic stir bar is centered in the vortex. Weigh 1.0 grams of a composition pressed or formed together as a single unit and add it to the water near the beaker edge but not touching the beaker edge. Begin a timer and allow the water with composition to stir for 1 minute.

Turn off the stirrer. Insert the conductivity probe into the water in a location away from any undissolved material. Allow a measurement to stabilize for a few seconds and record conductivity. Turn the stirrer back on. Restart the timer as the digital readout passes 250 rpm. After an additional 1 minute has elapsed, turn off the stirrer and measure and record conductivity in the same manner as above. Turn the stirrer back on. Restart the timer as the digital readout passes 250 rpm. Repeat the process until a conductivity reading has been obtained every minute of stirring, for 5 minutes.

After taking a 5 minute conductivity reading, cap the beaker with a suitable watertight cover, e.g., plastic wrap. Shake the beaker vigorously for about 1 minute to dissolve remaining solids, using a vortex type agitator and/or mild heating in addition if necessary until all soluble components are observed dissolved by visible inspection. Cool the solution to less than 80° F. prior to the final measurement. Uncap the beaker, measure conductivity and record the value as a final conductivity.

Calculate the fractional dissolution (f) at each time point by the equation: f=(conductivity−water conductivity)/(final conductivity−water conductivity)

Calculate the dissolution half-life by fitting the fractional dissolution time series (6 points from 0 to 5 minutes) to a second order polynomial and calculate an interpolated or extrapolated result for a time at which a composition is half dissolved (i.e., f=0.5).

Dissolution half-life can be a measure of the propensity of a composition to resist solubilization by water. Bars of soap, for example, can have a dissolution half-life of 21.1 minutes (Ivory®™ Soap), exhibiting longevity and low consumption rate during use without a need for substrates as barriers to permeability. Liquid body wash can have a dissolution half-life of less than ½ minute and can be unsuitable as a composition for some articles.

E. Compliance Test

To measure the compliance of a composition and/or article, use a Texture Analyzer TA-XT2i (Texture Technologies Corp, NY, USA) equipped with at least a 5 kg load cell and a 0.75 inch ball probe at ambient conditions, with the probe zero point at an article or composition top surface using 0.5 gram-force to register a probe height, and a 2 gram-force to commence data collection for both force and distance. Measure a compressive force (kg) at a compression rate of 1 mm/sec over a depth of 5 mm, ensuring the composition and/or article form a flat surface over contact area with the ball probe, near the center of the article or composition. Repeat measurements as needed (e.g. at least 3 times) to obtain a representative average value. To determine the compliance of the composition and/or article divide the maximum observed force (kg) by the maximum compression depth (5 mm). When using a 5 kg load cell some samples may exceed capacity, in this case the maximum compression depth will be less than the set depth of 5 mm, specified in the procedure.

VI. Examples

The following examples further describe and demonstrate some embodiments within the scope of the present invention. In the following examples, all ingredients are listed at an active level. The examples are given solely for the purpose of illustration and are not to be construed as limitations of the home care article or components thereof such as the composition or substrate, as many variations thereof are possible without departing from the spirit and scope disclosed herein.

A. Example Cleansing Compositions

Hand Dishwashing Cleansing Composition Examples

| | Examples (% w/w) | | | | |
|---|---|---|---|---|---|
| | 1 | 2 | 3 | 4 | 5 |
| Alkyl ethoxy sulfate $AE_xS$* | 28.0 | 28.0 | 25.0 | 27.0 | 20.0 |
| Amine oxide | 7.0 | 7.0 | 7.0 | 5.0 | 5.0 |
| $C_{9-11}$ $EO_8$ | — | — | — | 3.0 | 5.0 |
| Ethylan 1008 ® | — | — | 3.0 | — | — |
| Lutensol ® TO 7 | — | — | — | — | 5.0 |
| $GLDA^1$ | — | — | — | — | 1.0 |
| $DTPMP^2$ | — | — | — | — | 0.5 |
| $DTPA^3$ | — | — | 1.0 | — | — |
| $MGDA^4$ | — | — | — | 1.0 | — |
| Sodium citrate | — | — | 1.0 | — | 0.5 |
| Solvent | 2.5 | 2.5 | 4.0 | 3.0 | 2.0 |
| Polypropylene glycol ($M_n$ = 2000) | 1.0 | 1.0 | 0.5 | 1.0 | — |
| Sodium chloride | 0.5 | 0.5 | 1.0 | 1.0 | 0.5 |
| Water | to balance | to balance | to balance | to balance | to balance |

| | Examples (% w/w) | | | |
|---|---|---|---|---|
| | 6 | 7 | 8 | 9 |
| Alkyl ethoxy sulfate $AE_xS$* | 13 | 16 | 17 | 15 |
| Amine oxide | 4.5 | 5.5 | 6.0 | 5.0 |
| $C_{9-11}$ $EO_8$ | — | 2.0 | — | 5 |
| Ethylan 1008 ® | — | 2.0 | — | — |
| Lutensol ® TO 7 | 4 | — | 5 | — |
| $GLDA^1$ | 0.7 | 0.4 | 0.7 | 0.7 |
| $DTPMP^2$ | — | 0.3 | — | — |
| Sodium citrate | — | — | 0.2 | — |
| Solvent | 2.0 | 2.0 | 2.0 | 1.0 |
| Polypropylene glycol ($M_n$ = 2000) | 0.5 | 0.3 | 0.5 | 0.4 |
| Sodium chloride | 0.5 | 0.8 | 0.4 | 0.5 |
| Water | to balance | to balance | to balance | to balance |

| | Examples (% w/w) | | | |
|---|---|---|---|---|
| | 10 | 11 | 12 | 13 |
| Alkyl ethoxy sulfate $AE_xS$* | 16 | 29 | 18 | 20 |
| Amine oxide | 5.0 | 7.0 | 6.0 | 6.5 |
| $C_{9-11}$ $EO_8$ | 5 | — | — | 6.5 |
| Ethylan 1008 ® | — | — | — | — |
| Lutensol ® TO 7 | — | — | — | — |
| $GLDA^1$ | 0.7 | — | — | 1.0 |
| $DTPMP^2$ | — | — | — | — |
| Sodium citrate | — | — | 2.5 | — |
| Solvent | 1.3 | 4.0 | — | 2.0 |
| Polypropylene glycol ($M_n$ = 2000) | 0.5 | 1.0 | 1.0 | 0.4 |
| Sodium chloride | 0.8 | 1.5 | 0.5 | 0.5 |
| Water | to balance | to balance | to balance | to balance |

*Number of carbon atoms in the alkyl chain is between 12 and 13; and x is between 0.5 and 2.
Ethylan 1008 ® is a nonionic surfactant based on a synthetic primary alcohol, commercially available from Akzo Nobel.
Lutensol ® TO 7 is nonionic surfactant made from a saturated iso-$C_{13}$ alcohol.
Solvent is ethanol.
Amine oxide is coconut dimethyl amine oxide.
$^1$Glutamic-N,N-diacetic acid
$^2$Diethylenetriamine penta methylphosphonic acid
**Examples may have other optional ingredients such as dyes, opacifiers, perfumes, preservatives, hydrotropes, processing aids, salts, stabilizers, etc.

Hard Surface Cleansing Example Compositions

The following examples will further illustrate the present invention. The compositions are made by combining the listed ingredients in the listed proportions (weight % unless otherwise specified). The following Examples are meant to exemplify compositions used in a process according to the present invention but are not necessarily used to limit or otherwise define the scope of the present invention.

|                    | A     | B     | C     | D    | E    | F    | G     | H     | I    |
|--------------------|-------|-------|-------|------|------|------|-------|-------|------|
| Non ionic          |       |       |       |      |      |      |       |       |      |
| C9/11 EO 8         | 6.0   | 6.0   | 7.0   |      |      | 6.0  | 6.0   | 6.0   | 6.2  |
| C9/11 EO 5         |       |       |       | 3.5  |      |      |       |       |      |
| C12/14 EO21        |       |       |       | 3.5  |      |      |       |       |      |
| C11 EO 5           |       |       |       |      | 7.0  |      |       |       |      |
| Anionic            |       |       |       |      |      |      |       |       |      |
| NaLAS              | 2.00  | 2.25  | 1.8   |      |      |      | 1.80  | 2.25  | 1.80 |
| NAPS               |       |       |       | 3.1  | 3.0  | 3.0  |       |       | 3.1  |
| C12-14AS           |       |       |       |      |      |      |       |       |      |
| NaCS               |       |       |       |      |      |      |       |       |      |
| Co surfactants     |       |       |       |      |      |      |       |       |      |
| C12-14 AO          | 1.50  | 1.25  | 1.50  | 3.9  | 2.0  |      | 1.50  | 1.25  | 1.50 |
| C12-14 Betaine     |       |       |       |      | 1.0  | 3.0  |       |       |      |
| Thickeners         |       |       |       |      |      |      |       |       |      |
| HM-polyacrylate    | 0.76  | 0.65  | 0.75  |      |      |      | 0.70  | 0.65  | 0.65 |
| HM-HEC             |       |       |       | 0.6  | 0.8  |      |       |       |      |
| X gum              |       |       |       |      |      | 0.42 |       |       |      |
| Buffer             |       |       |       |      |      |      |       |       |      |
| Na2CO3             | 0.77  | 0.4   | 0.75  | 0.1  | 0.3  | 0.2  | 0.75  | 0.4   | 0.75 |
| Citric Acid        | 0.046 | 0.3   | 0.3   | 0.75 | 0.75 | 0.3  | 0.3   | 0.3   | 0.30 |
| Caustic            | 0.46  | 0.76  | 0.72  | 0.5  | 0.5  | 0.3  | 0.65  | 0.65  | 0.60 |
| Suds Control       |       |       |       |      |      |      |       |       |      |
| Fatty Acid         | 0.40  | 1.0   | 1.0   | 0.20 | 0.50 | 0.50 | 0.40  | 0.40  | 1.0  |
| Branched fatty alcohols |  |       |       |      |      |      |       |       |      |
| Isofol 12          |       | 0.2   | 0.1   | 0.2  | 0.3  | 0.5  |       |       | 0.1  |
| Isofol 16          |       |       |       |      |      |      |       |       |      |
| Chelants           |       |       |       |      |      |      |       |       |      |
| DTPMP              |       | 0.3   | 0.30  |      |      | 0.2  |       |       | 0.3  |
| DTPA               | 0.25  |       |       |      |      |      | 0.25  | 0.25  |      |
| GLDA               |       |       |       |      |      |      |       |       |      |
| Solvents           |       |       |       |      |      |      |       |       |      |
| IPA                |       |       |       |      |      | 2.0  |       |       |      |
| n-BPPP             |       |       |       |      | 2.0  |      |       |       |      |
| N-BP               |       |       |       | 4.0  | 2.0  |      |       | 2.0   |      |
| Minors and Water   | up to 100% | up to 100% | up to 100% | up to 100% | up to 100% | up to 100% | up to 100% | upto 100% | up to 100% |
| pH                 | 10.6  | 10.5  | 10.3  | 9.5  | 9.0  | 10.0 | 10.3  | 10.5  | 10.3 |

$C_{9-11}$ $EO_5$ is a $C_{9-11}$ $EO_5$ nonionic surfactant commercially available from ICI or Shell. $C_{12,14}$ $EO_5$ is a $C_{12,14}$ $EO_5$ nonionic surfactant commercially available from Huls, A&W or Hoechst. $C_{11}$ $EO_5$ is a $C_{11}$ $EO_5$ nonionic surfactant. $C_{12,14}$ $EO_{21}$ is a $C_{12,14}$ $EO_{21}$ nonionic surfactant. NaPS is Sodium Paraffin sulphonate commercially available from Huls or Hoechst. NaLAS is Sodium Linear Alkylbenzene sulphonate commercially available from A&W. NaCS is Sodium Cumene sulphonate commercially available from A&W. Isalchem ® AS is a $C_{12-13}$ sulphate surfactant commercially available from Sasol olefins and surfactants. $C_{12-14}$ AO is a $C_{12-14}$ amine oxide surfactant. $C_{12-14}$ Betaine is a $C_{12-14}$ betaine surfactant.

DMPEG is a polyethyleneglycol dimethylether. HM-HEC is a cetylhydroxethylcellulose. Isofol 12® is 2-butyl octanol commercially available from Condea. Isofol 16® is 2-hexyl decanol commercially available from Condea. n-BP is normal butoxy propanol commercially available from Dow Chemicals. IPA is isopropanol. n-BPP is butoxy propoxy propanol available from Dow Chemicals.

B. Example Substrates

1. Formed Films

| Material Description | Caliper and Basis Weight | Pore count/area; and diameter | Water Flux Rate cc/cm$^2$/s | Air Permeability m$^3$/m$^2$/s |
|---|---|---|---|---|
| Hydroapertured polyethylene film on 100 mesh screen, white (Tredegar Inc.) | 166 microns, 24.5 gsm | 1,780/cm$^2$ — | 6.2 | 58 |
| Vacuum formed polyethylene film, white (SSRIS-CPM, Tredegar Inc.) | 560 microns, 24.5 gsm | 115/cm$^2$ — | 33.8 | 295 |
| Vacuum formed polyethylene film, white 22 Hex (Tredegar, Inc.) | 560 microns, 24.4 gsm | 91/cm$^2$ ~500 micron | — | 130 |
| Vacuum formed polyethylene | 935 | 22.2/cm$^2$ | — | 145 |

| Material Description | Caliper and Basis Weight | Pore count/area; and diameter | Water Flux Rate cc/cm²/s | Air Permeability m³/m²/s |
|---|---|---|---|---|
| film, blue 11.2 Hex (Tredegar, Inc.) | microns, 29.4 gsm | 1.1 mm | | |
| Vacuum formed polyethylene film, green (Tredegar, Inc.) | 670 microns, 36.0 gsm | 49/cm² 0.9 mm | — | 220 |
| Vacuum formed polyethylene film, white (Tredegar, Inc.) | 33.5 gsm — | 12.6/cm² 1 mm | — | — |
| Vacuum formed polyethylene film 40 Hex | 418 microns, 35.8 gsm | 285/cm² — | 11.5 | 16.2 |

Caliper: ASTM D645
Air Permeability: ASTM D737

2. Fibrous Nonwovens

| Material Description | Basis Weight | Water Flux Rate cc/cm²/s |
|---|---|---|
| Spunlaid hydroentangled 100% PP (Avgol Nonwovens, NC, USA) | 47 gsm | 6.0 |
| Carded, calendar bonded all bicomponent PP/PE fiber (Fiberweb Inc., TN, USA) | 32 gsm | 20.7 |
| Spunbond, overbonded 100% PP (Experimental nonwoven) | 37 gsm | 2.1 |
| Carded, through air bonded 30/30/40 PP/Bicomponent PP-PE/Rayon (calendar patterned) | 62 gsm | 2.8 |

3. Fibrous Nonwoven Battings

| Material Description | Caliper; and Basis Weight | Water Permeability cc/cm²/s |
|---|---|---|
| Quilter's Fusible batting, low loft all polyester (Fairfield Processing, Danbury, CT, USA) | 2.50 mm, 160 gsm | 58.3 |
| Quilter's Fusible batting, low loft all polyester, ½ thickness (peeled) | 1.21 mm, 80 gsm | 71.3 |
| PROEF 12-334 polyester-bicomponent fiber blend batting (Libeltex, Belgium) | 1.54 mm, 100 gsm | — |
| PROEF 12-370 dual layer PET/copet bico and PP fibers; bulk layer with standard PET/coPET bico trilobal fibers (Libeltex, Belgium) | 0.60 mm, 55 gsm | — |
| Dry Web T30 SC batting, hollow PET + bico PET/PE fiber blend, through air bonded (Libeltex, Belgium) | 0.41 mm, 35 gsm | — |
| PROEF 12-372 batting, coarse polyester and PE/PET bico fibers (Libeltex, Belgium) | 0.55 mm, 50 gsm | — |
| Dry Web T23W batting, coarse polyester and bico fiber mix (Libeltex, Belgium) | 0.56 mm, 50 gsm | — |

Caliper measured at 0.8 grams/mm²

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing article, comprising:
   a. a compliant cleansing composition having a first side and a second side;
   b. a first substrate adjacent to one side of the cleansing composition;
   c. a second substrate adjacent to the other side of the cleansing composition;
   d. a first water insoluble substrate adjacent to the first substrate, and
   e. a second water insoluble substrate adjacent to the second substrate;
   f. wherein the composition has a compliance of about 0.03 to about 1.50 kg/mm.

2. The cleansing article of claim 1, wherein the first and second substrates form a pouch around the cleansing composition.

3. The cleansing article of claim 2, wherein the composition is greater than 3,500 wt %, by weight of the total substrate.

4. The cleansing article of claim 2, wherein the composition is greater than 4,000 wt %, by weight of the total substrate.

5. The cleansing article of claim 4, wherein at least one substrate has a water flux rate of 20 cm³/cm²/s or more.

6. The cleansing article of claim 5, wherein the article has a consumption rate of about 1.5 g/use to about 15 g/use.

7. The cleansing article of claim 1, wherein the first and second substrates comprise a formed film.

8. The cleansing article of claim 7, wherein the first and second substrates are water penetrable.

9. The cleansing article of claim 1, wherein the first water insoluble substrate comprises a laminate.

10. The cleansing article of claim 9, wherein the laminate comprises a nonwoven and a formed film.

11. The cleansing article of claim 1, wherein the first water insoluble substrate, second water insoluble substrate, or a combination thereof, are a contact substrate.

12. The cleansing article of claim 11, wherein the contact substrate is adapted for contacting the skin.

13. The cleansing article of claim 1, wherein the cleansing composition comprises particles.

14. The cleansing article of claim 1, wherein the cleansing composition comprises a preservative.

15. The cleansing article of claim 1, wherein the cleansing composition is in the form of pellets, bar, paste, gel, or a combination thereof.

16. The cleansing article of claim 1, wherein the article is compliant.

17. The cleansing article of claim 16, wherein the article has a compliance of about 0.03 kg/mm to about 1.50 kg/mm.

18. The cleansing article of claim 16, wherein the article has a compliance of about 0.05 kg/mm to about 1.15 kg/mm.

19. The cleansing article of claim 16, wherein the article has a compliance of about 0.10 kg/mm to about 1.1 kg/mm.

20. The cleansing article of claim 16, wherein the composition has a compliance of about 0.05 kg/mm to about 1.15 kg/mm.

21. The cleansing article of claim 16, wherein the composition has a compliance of about 0.10 kg/mm to about 1.1 kg/mm.

22. The cleansing article of claim 16, wherein the composition comprises micro fibril cellulose.

23. The cleansing article of claim 21, wherein the first and second substrates comprise the same formed film.

24. The cleansing article of claim 23, wherein the formed film comprises polyolefin.

25. The cleansing article of claim 24, wherein the first substrate, second substrate, or both substrates, are water penetrable.

26. The cleansing article of claim 25, wherein the first water insoluble substrate comprises a laminate.

27. The cleansing article of claim 26, wherein the laminate comprises a nonwoven and a formed film.

28. The cleansing article of claim 27, wherein the first water insoluble substrate, second water insoluble substrate, or a combination thereof, are a contact substrate.

29. The cleansing article of claim 28, wherein the contact substrate is adapted for contacting the skin.

30. The cleansing article of claim 29, wherein the cleansing composition comprises a preservative.

31. The cleansing article of claim 30, wherein the cleansing composition comprises particles.

32. The cleansing article of claim 30, wherein the article has a compliance of about 0.03 kg/mm to about 1.50 kg/mm.

33. The cleansing article of claim 30, wherein the article has a compliance of about 0.05 kg/mm to about 1.15 kg/mm.

34. The cleansing article of claim 30, wherein the article has a compliance of about 0.10 kg/mm to about 1.1 kg/mm.

35. The cleansing article of claim 34, wherein the composition is greater than 3,500 wt %, by weight of the total substrate.

36. The cleansing article of claim 34, wherein the composition is greater than 4,000 wt %, by weight of the total substrate.

37. The cleansing article of claim 1, wherein the composition is greater than 3,500 wt %, by weight of the total substrate.

38. The cleansing article of claim 1, wherein the composition is greater than 4,000 wt %, by weight of the total substrate.

* * * * *